(12) United States Patent
Lei et al.

(10) Patent No.: US 10,537,503 B2
(45) Date of Patent: Jan. 21, 2020

(54) MICROCAPSULE COMPOSITIONS WITH HIGH PERFORMANCE

(71) Applicant: International Flavors & Fragrances Inc., New York, NY (US)

(72) Inventors: Yabin Lei, Holmdel, NJ (US); Li Xu, Edison, NJ (US); John Brahms, Morris Plains, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 15/556,111

(22) PCT Filed: Mar. 4, 2016

(86) PCT No.: PCT/US2016/020995
§ 371 (c)(1),
(2) Date: Sep. 6, 2017

(87) PCT Pub. No.: WO2016/144798
PCT Pub. Date: Sep. 15, 2016

(65) Prior Publication Data
US 2018/0042825 A1    Feb. 15, 2018

Related U.S. Application Data

(60) Provisional application No. 62/129,431, filed on Mar. 6, 2015.

(51) Int. Cl.
| | | |
|---|---|---|
| A61K 8/11 | (2006.01) | |
| A01N 25/28 | (2006.01) | |
| A61K 8/73 | (2006.01) | |
| A61K 8/81 | (2006.01) | |
| A61K 8/84 | (2006.01) | |
| A61Q 1/12 | (2006.01) | |
| A61Q 5/06 | (2006.01) | |
| A61Q 5/12 | (2006.01) | |
| A61Q 13/00 | (2006.01) | |
| A61Q 15/00 | (2006.01) | |
| A61Q 19/00 | (2006.01) | |
| A61Q 19/10 | (2006.01) | |
| B01J 13/18 | (2006.01) | |
| C11B 9/00 | (2006.01) | |

(52) U.S. Cl.
CPC ............... *A61K 8/11* (2013.01); *A01N 25/28* (2013.01); *A61K 8/732* (2013.01); *A61K 8/8176* (2013.01); *A61K 8/84* (2013.01); *A61Q 1/12* (2013.01); *A61Q 5/06* (2013.01); *A61Q 5/12* (2013.01); *A61Q 13/00* (2013.01); *A61Q 15/00* (2013.01); *A61Q 19/001* (2013.01); *A61Q 19/007* (2013.01); *A61Q 19/10* (2013.01); *B01J 13/18* (2013.01); *C11B 9/00* (2013.01); *A61K 2800/624* (2013.01); *A61K 2800/63* (2013.01)

(58) Field of Classification Search
None
See application file for complete search history.

(56) References Cited

U.S. PATENT DOCUMENTS

| | | | | |
|---|---|---|---|---|
| 2007/0042182 A1* | 2/2007 | Markus | ................. | A01N 65/00 428/402.2 |
| 2011/0071064 A1* | 3/2011 | Lei | ............................ | A61K 8/11 510/119 |
| 2014/0017287 A1* | 1/2014 | Lei | ........................... | B01J 13/14 424/401 |

* cited by examiner

*Primary Examiner* — Bong-Sook Baek
(74) *Attorney, Agent, or Firm* — Martin Z. Zhang; Xufan Tseng; Elizabeth M. Stover

(57) ABSTRACT

A microcapsule composition is provided, which contains a polyurea or polyurethane microcapsule, an alkylnaphthalenesulfonate formaldehyde condensate, and polyvinylpyrrolidone. Also disclosed is a process of preparing the microcapsule composition and a consumer product having such a microcapsule composition.

15 Claims, No Drawings

MICROCAPSULE COMPOSITIONS WITH HIGH PERFORMANCE

CROSS REFERENCE TO RELATED APPLICATIONS

This application is a national stage entry under 35 USC 371 for International Application No. PCT/US2016/020995, filed on Mar. 4, 2016. The international application claims priority to US Patent Application, Serial Nos. 62/129,431, filed on Mar. 6, 2015, the content of which is incorporated herein by reference in its entirety.

BACKGROUND

Microcapsules are used in a variety of different applications where there is a need to deliver, apply, or release an active material including a fragrance, flavor, and malodor counteraction agent to a target area in a time-delayed or controlled manner. Various techniques for preparing capsules are known in the art and are used, depending on the contents to be encapsulated, the environment in which the capsules should retain their integrity and the desired release mechanism.

Interfacial polycondensation is a known technique for preparing capsules and versatile capsule wall materials are used including polyureas and polyurethanes (WO 2011/154893, WO 2012/107323, US 2011/0077188, U.S. Pat. Nos. 5,635,211, 6,586,107, and 6,797,670). Such wall materials are produced by having a first phase which is water-immiscible and includes a polyfunctional isocyanate, i.e., a polyisocyanate having two or more isocyanate groups, and a second aqueous phase which includes (i) a polyfunctional alcohol (i.e., a polyol) having two or more —OH groups, or (ii) a polyfunctional amine (i.e., a polyamine) having two or more —NH$_2$ and/or —NH groups.

Raw materials and processes for preparing capsules by polycondensation are described in U.S. Pat. No. 4,640,709 and the publications described therein. As is exemplified therein, and also in U.S. Pat. No. 6,133,197, polyurea and polyurethane capsules are often used for rugged applications, such as for encapsulation of agrochemicals, e.g., herbicides and pesticides, where slow time-release is desired to set the agents free. For such applications, the capsules also require a relatively high mechanical strength. For the polycondensation reaction, suitable diisocyanate and symmetrical triisocyanate starting materials are disclosed in the prior art.

WO 2011/154893 discloses a process for the preparation of capsules, which includes mixing at least one aliphatic polyisocyanate and of at least one aromatic polyisocyanate, wherein the molar ratio between the two polyisocyanates is between 75:25 and 20:80.

WO 2013/000587 discloses a process for the preparation of polyurea capsules, which includes dissolving at least one polyisocyanate having at least two isocyanate functional groups, in a perfume to form a solution; adding to the solution an aqueous solution of an emulsifier or of a colloidal stabilizer; and adding to the mixture to 3,5-diamino-1,2,4-triazole to form a polyurea wall.

U.S. Pat. No. 5,304,448 describes an encapsulated toner composition using reaction of amino acids and polyisocyanates.

Known polyurea or polyurethane capsules face various issues, e.g., low olfactory intensity.

There is a need to develop capsules with high performance for use in laundry, washing, cleaning, surface care and personal and skin care. For such applications quicker and easier release and/or less mechanical strength are often desirable. Also, it would be desirable to more precisely influence the capsule wall permeability and other capsule wall properties to achieve the desired release profile and consumer benefits.

SUMMARY OF THE INVENTION

This invention is based on the discovery that certain microcapsule compositions possess unexpected desirable properties including high performance.

Accordingly, one aspect of this invention relates to a microcapsule composition containing (i) polyurea or polyurethane microcapsules, (ii) an alkylnaphthalenesulfonate formaldehyde condensate, and (iii) polyvinylpyrrolidone. In this composition, each of the microcapsules has a microcapsule core containing an active material and a microcapsule wall containing a polyurea or polyurethane, and the microcapsule wall encapsulates the microcapsule core. Typically, the microcapsule core is at a level of 5 to 99.9% (e.g., 35 to 99.9%) by weight of the composition and the capsule wall is at a level of 0.1 to 95% (e.g., 0.1 to 65%).

The active material contained in the microcapsule wall can be a fragrance, pro-fragrance, flavor, malodor counteractive agent, anti-inflammatory agent, anesthetic, analgesic, anti-viral agent, anti-infectious agent, anti-acne agent, skin lightening agent, insect repellant, emollient, skin moisturizing agent, vitamin or derivative thereof, nanometer to micron size inorganic solid, polymeric or elastomeric particle, or combination thereof.

As the microcapsule wall material, the polyurea typically is a reaction product of a polyfunctional isocyanate and a polyfunctional amine as a cross-linking agent in the presence of an alkylnaphthalenesulfonate formaldehyde condensate and polyvinylpyrrolidone. Other wall material can be polyurethane, which typically is a reaction product of a polyfunctional isocyanate and a polyfunctional alcohol as a cross-linking agent in the presence of an alkylnaphthalenesulfonate formaldehyde condensate and polyvinylpyrrolidone.

Suitable polyfunctional isocyanates include an aromatic polyfunctional isocyanate, aliphatic polyfunctional isocyanate, or combination thereof. The aromatic polyfunctional isocyanate can contain a phenyl, tolyl, xylyl, naphthyl, or diphenyl moiety, or a combination thereof and the aliphatic polyfunctional isocyanate can be a trimer of hexamethylene diisocyanate, a trimer of isophorone diisocyanate, a biuret of hexamethylene diisocyanate, or a combination thereof.

Exemplary aromatic polyfunctional isocyanates are polyisocyanates of toluene diisocyanate, trimethylol propane-adducts of toluene diisocyanate, and trimethylol propane-adducts of xylylene diisocyanate. Preferably, it is polymeric methylene diphenyl diisocyanate. Suitable aliphatic polyfunctional isocyanates include those selected from the group consisting of dimers, biurets, symmetric trimers, asymmetric trimers of hexamethylene diisocyanate.

As crosslinking agents, suitable polyfunctional amines include hexamethylene diamine, ethylenediamine, 1,3-diaminopropane, 1,4-diamino-butane, diethylenetriamine, pentaethylenehexamine, 1,6-diaminohexane, hydrazine, 1,4-diaminocyclohexane and 1,3-diamino-1-methylpropane, bis(3-aminopropyl)amine, bis(hexanethylene)triamine, tris (2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, or a combination thereof.

In any of the microcapsule compositions described above, the alkylnaphthalenesulfonate formaldehyde condensate and polyvinylpyrrolidone can constitute 0.1 to 5% (e.g., 0.2 to 4% and 0.3 to 3%) of the microcapsule composition. The ratio between the alkylnaphthalene-sulfonate formaldehyde condensate and polyvinylpyrrolidone is 10:1 to 1:10 (e.g., 5:1 to 1:5, 2:1 to 1:4, and 1:1 to 1:3).

Suitable polyvinylpyrrolidones have an average molecular weight of 1,000 to 10,000,000 (e.g., 2,000 to 5,000,000 and 5,000 to 1,500,000).

In addition to polyvinylpyrrolidones and alkylnaphthalenesulfonate formaldehyde condensates, microcapsule compositions of this invention can further contain a polyvinyl alcohol, polystyrene sulfonate, carboxymethyl cellulose, copolymer of vinyl pyrrolidone and quaternized dimethylaminoethyl methacrylate, or mixture thereof.

Any microcapsule composition described above can further contain a stabilizing agent selected from the group consisting of hexamethylene diamine, ethylenediamine, 1,3-diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diaminoguanidine, 1,1-dimethylbiguanide, guanidine, arginine, lysine, ornithine, histidine, amino-2-methyl-1-propanol, and a combination thereof.

In certain embodiments, any microcapsule compositions described above contains deposition aid that is an anionic, cationic, nonionic or zwitterionic polymer. Examples include polyquaternium-6, polyquaternium-22, polyquaternium-39, polyquaternium-47, polyvinylamine, polyethyleneimine, polyvinylamine and vinylformamide copolymer, or a mixture thereof.

The microcapsules in any of the compositions of this invention can be purified by washing the microcapsules with water or an aqueous solution. These microcapsules can also be cured at a temperature of 35° C. or greater (e.g., 55° C. or greater).

Some embodiments of the microcapsule compositions contain one or more additional microcapsules (e.g., a second, third, fourth, fifth, or sixth microcapsule). The one or more additional microcapsules are different from each other in term of microcapsule size, microcapsule wall forming polymer, or encapsulated active material.

Free active materials (e.g., unencapsulated fragrances or flavors) can also be included in the composition.

The microcapsule compositions of this invention can be in a dry form (e.g., spray-dried) or in a slurry (e.g., containing 30 to 70% water).

In a slurry, the microcapsule is dispersed in a water phase. In a dry form, the microcapsule can be coated in a starch, or dispersed in a starch matrix. Typically, a free active material is also included in the starch.

Another aspect of this invention related to a process of preparing any one of the microcapsule composition described above. The process includes the steps of: (i) preparing an oil phase having an active material and a multi-functional isocyanate; (ii) preparing an aqueous phase having (i) an alkylnaphthalenesulfonate formaldehyde condensate, (ii) polyvinylpyrrolidone, (iii) emulsifying the oil phase into the aqueous phase to form an active emulsion; (iv) adding to the active emulsion a crosslinking agent that is a multi-functional amine or multi-functional alcohol to form a reaction emulsion; (v) causing formation of polyurea or polyurethane microcapsules in the reaction emulsion to obtain a microcapsule slurry; and (vi) curing the microcapsule slurry, thereby obtaining a microcapsule composition. Curing can be achieved at a temperature of greater than 35° C. (e.g., 55° C. or greater).

Also within the scope of this invention is a consumer product containing a microcapsule composition described above. Exemplary consumer products include a shampoo, a hair conditioner, a hair rinse, a hair refresher, a hair fixative or styling aid, a hair bleach, a hair dye or colorant, a soap, a body wash, a cosmetic preparation, an all-purpose cleaner, a bathroom cleaner, a floor cleaner, a window cleaner, a bath tissue, a paper towel, a disposable wipe, a diaper rash cream or balm, a baby powder, a diaper, a bib, a baby wipe, an oral care product, a tooth paste, an oral rinse, an tooth whitener, a denture adhesive, a chewing gum, a breath freshener, an orally dissolvable strips, a chewable candy, a hard candy, a hand sanitizer, an anti-inflammatory balm, an anti-inflammatory ointment, an anti-inflammatory spray, a health care device, a dental floss, a toothbrush, a tampon, a feminine napkin, a personal care product, a sunscreen lotion, a sunscreen spray, a wax-based deodorant, a glycol type deodorant, a soap type deodorant, a facial lotion, a body lotion, a hand lotion, a body powder, a shave cream, a bath soak, an exfoliating scrib, a foot cream, a facial tissue, a cleansing wipe, a fabric care product, a fabric softener, a fabric refresher, an ironing water, a liquid laundry detergent, a liquid dish detergent, an automatic dish detergent, a unit dose tablet or capsule, a scent booster, a drier sheet, a fine fragrance, a solid perfume, a powder foundation, a liquid foundation, an eye shadow, a lipstick or lip balm, an Eau De Toilette product, a deodorant, a rug deodorizer, a candle, a room deodorizer, a disinfectant, an anti-perspirant, an roll-on product, an aerosol product, a baked product, a bread, a dry biscuit, a cake, a cookie, a chip, a popcorn, a pretzel, an extruded snack, a breakfast cereal, a mueli bar, a precooked finished rice product, an alcoholic or non-alcoholic beverage, a spice blend, a soup, a sauce, a stew, a frozen entrée, a yogurt, an ice cream, a bean curd, a cheese, a soya protein product, a meat product, an egg product, a mayonnaise, a remoulade, a dressing, a seasoning preparation, a fruit preparation, and a vegetable preparation.

More examples are an aerosol antiperspirant, a stick antiperspirant, a roll-on antiperspirant, an emulsion spray antiperspirant, a clear emulsion stick antiperspirant, a soft solid antiperspirant, an emulsion roll-on antiperspirant, a clear emulsion stick antiperspirant, an opaque emulsion stick antiperspirant, a clear gel antiperspirant, a clear stick deodorant, and a spray deodorant. Preferably, it is a shampoo, a hair conditioner, a hair rinse, a hair refresher, a body wash, or a soap.

The details of one or more embodiments of the invention are set forth in the description below. Other features, objects, and advantages of the invention will be apparent from the description and the claims.

DETAILED DESCRIPTION OF THE INVENTION

It has been found that polyurea/polyurethane microcapsule compositions prepared with a combination of an alkylnaphthalenesulfonate formaldehyde condensate and polyvinylpyrrolidone are suitable for carrying various kinds of hydrophobic or hydrophilic active materials of use in products intended for application to animate and inanimate surfaces.

Polyurea/polyurethane microcapsule compositions of this invention are useful in a wide range of consumer applications, e.g., personal care products including shampoo, hair conditioners, personal wash such as soaps, body wash, personal cleaners and sanitizers, fabric care such as fabric refreshers, softeners and dryer sheets, ironing water, industrial cleaners, liquid and powder detergent including unit dose capsules, rinse conditioners, scent booster products, fine fragrances, an Eau De Toilette product, a deodorant, an roll-on product, or an aerosol product.

More specifically, the capsule compositions of this invention are well-suited for use in an aerosol antiperspirant, a stick antiperspirant, a roll-on antiperspirant, an emulsion spray antiperspirant, a clear emulsion stick antiperspirant, a soft solid antiperspirant, an emulsion roll-on antiperspirant, a clear emulsion stick antiperspirant, an opaque emulsion stick antiperspirant, a clear gel antiperspirant, a clear stick deodorant, or a spray deodorant. Moreover, these microcapsule compositions provide great benefits in a shampoo, a hair conditioner, a hair rinse, a hair refresher, a body wash, or a soap.

Suitable microcapsule compositions can be prepared by reacting a polyisocyanate with a cross-linking agent in the presence of an alkylnaphthalenesulfonate formaldehyde condensate and polyvinylpyrrolidone so that an active material is encapsulated in an oil core by a capsule wall. The oil core optionally contains a core modifier.

These capsule-forming materials are described in detail below.

Polyisocyanate.

The polyurea or polyurethane capsules of this invention are prepared using one or more polyisocyanates. Each of them has two or more isocyanate groups, i.e., O=C=N—, wherein said polyisocyanate can be aromatic, aliphatic, linear, branched, or cyclic. In certain embodiments, the polyisocyanate contains, on average, 2 to 4 —N=C=O groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

In other embodiments, the polyisocyanate is an aliphatic polyisocyanate. In certain embodiments, the aliphatic polyisocyanate is a trimer of hexamethylene diisocyanate, a trimer of isophorone diisocyanate or a biuret of hexamethylene diisocyanate. Exemplary aliphatic polyisocyanates include those commercially available, e.g., BAYHYDUR N304 and BAYHYDUR N305, which are aliphatic water-dispersible polyisocyanates based on hexamethylene diisocyanate; DESMODUR N3600, DESMODUR N3700, and DESMODUR N3900, which are low viscosity, polyfunctional aliphatic polyisocyanates based on hexamethylene diisocyanate; and DESMODUR 3600 and DESMODUR N100 which are aliphatic polyisocyanates based on hexamethylene diisocyanate, each of which is available from Bayer Corporation, Pittsburgh, Pa.).

One class of suitable polyisocyanates are aromatic polyisocyanates that have the generic structure below (i.e., polymeric methylene diphenyl diisocyanate or PMDI, and its structural isomers

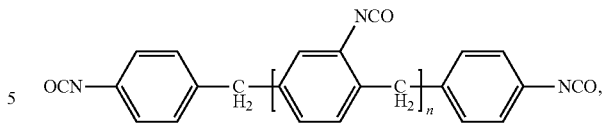

wherein n can vary from zero to a desired number depending on the type of polyamine or polyol used. Preferably, n is less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5.

Specific examples of wall monomer isocyanates include, for example, 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanato-cyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, 3,3-bischloromethyl ether 4,4'-diphenyldiisocyanate. Sulfur-containing polyisocyanates are obtained, for example, by reacting 2 mol of hexamethylene diisocyanate with 1 mol of thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

Other suitable commercially-available polyisocyanates include LUPRANATE M20 (polymeric methylene diphenyl diisocyanate, "PMDI" commercially available from BASF containing isocyanate group "NCO" 31.5 wt %), where the average n is 0.7; PAPI 27 (PMDI commercially available from Dow Chemical having an average molecular weight of 340 and containing NCO 31.4 wt %) where the average n is 0.7; MONDUR MR (PMDI containing NCO at 31 wt % or greater, commercially available from Bayer) where the average n is 0.8; MONDUR MR Light (PMDI containing NCO 31.8 wt %, commercially available from Bayer) where the average n is 0.8; MONDUR 489 (PMDI commercially available from Bayer containing NCO 30-31.4 wt %) where the average n is 1.0; poly[(phenylisocyanate)-co-formaldehyde] (Aldrich Chemical, Milwaukee, Wis.), other isocyanate monomers such as DESMODUR N3200 (poly(hexamethylene diisocyanate) commercially available from Bayer), and TAKENATE D110-N (xylene diisocyanate adduct polymer commercially available from Mitsui Chemicals corporation, Rye Brook, N.Y., containing NCO 11.5 wt %).

In particular embodiments, an exemplary polyisocyanate has the following structure:

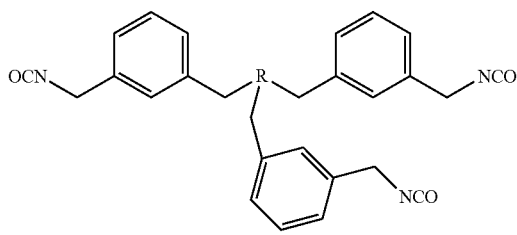

or its structural isomer. Representative polyisocyanates are TAKENATE D-110N (a polyisocyanate based on xylene diisocyanate commercially available from Mitsui), DESMODUR L75 (a polyisocyanate base on toluene diisocyanate commercially available from Bayer), and DESMODUR IL (another polyisocyanate based on toluene diisocyanate commercially available from Bayer).

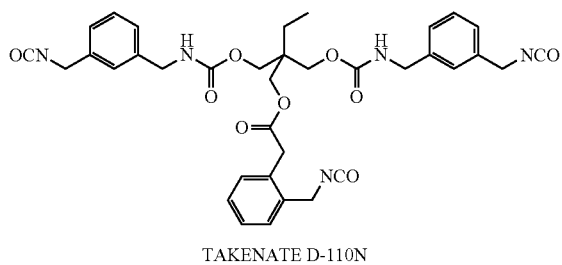

TAKENATE D-110N

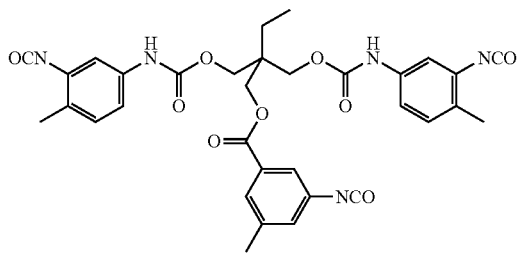

DESMODUR L75

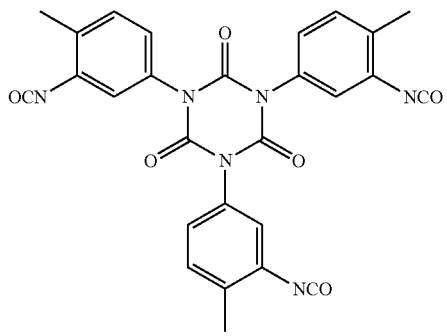

DESMODUR IL

In some embodiments, the polyisocyanate used in the preparation of the polyurea or polyurethane capsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea compositions of this invention.

The average molecular weight of certain polyisocyanates useful in this invention varies from 250 to 1000 Da and preferable from 275 to 500 Da. In general, the range of the polyisocyanate concentration in the composition of this invention varies from 0.1% to 10%, preferably from 0.1% to 8%, more preferably from 0.2 to 5%, and even more preferably from 1.5% to 3.5%, all based on the total capsule composition.

More examples of suitable isocyanates can be found in PCT 2004/054362; EP 0 148149; EP 0 017 409 B1; U.S. Pat. Nos. 4,417,916, 4,124,526, 5,583,090, 6,566,306, 6,730,635, PCT 90/08468, PCT WO 92/13450, U.S. Pat. Nos. 4,681,806, 4,285,720 and 6,340,653.

Cross-Linking Agent.

Cross-linking agents are used to form the capsule walls. These agents in general contains multiple (i.e., two or more) function groups (e.g., —NH—, —NH$_2$ and —OH) that can react with polyisocyanates to form polyureas or polyurethanes. Examples include multi-functional amines (e.g., polyamines) and multi-functional alcohols (e.g., polyols).

Suitable polyamines contain two or more amine groups including —NH$_2$ and —R*NH, R* being substituted and unsubstituted $C_1$-$C_{20}$ alkyl, $C_1$-$C_{20}$ heteroalkyl, $C_1$-$C_{20}$ cycloalkyl, 3- to 8-membered heterocycloalkyl, aryl, and heteroaryl.

Two classes of such polyamines include polyalkylene polyamines having the following structures:

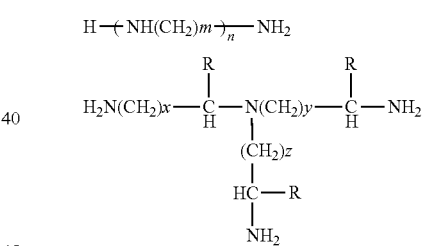

In which R is hydrogen or —CH$_3$; and m, n, x, y, and z each are integers from 0-2000 (e.g., 1, 2, 3, 4, and 5). Examples include ethylene diamine, 1,3-diaminepropane, diethylene triamine, triethylene tetramine, 1,4-diaminobutane, hexaethylene diamine, hexamethylene diamine, pentaethylenehexamine, and the like.

Another class of polyamines are polyalkylene polyamines of the type:

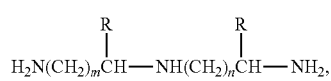

where R equals hydrogen or —CH$_3$, m is 1-5 and n is 1-5, e.g., diethylene triamine, triethylene tetramine and the like. Exemplary amines of this type also include diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

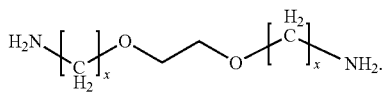

Exemplary polyetheramines include 2,2'-ethylenedioxy)bis (ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, D-lysine, L-arginine, D-arginine, L-lysine monohydrochloride, D-lysine monohydrochloride, L-arginine monohydrochloride, D-arginine monohydrochloride, L-ornithine monohydrochloride, D-ornithine monohydrochloride or a mixture thereof.

Guanidine amines and guanidine salts are yet another class of multi-functional amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 having a structure shown above (where x=2), JEFFAMINE EDR-176 (where x=3) (from Huntsman). Other polyether amines include the JEFFAMINE ED Series, JEFFAMINE TRIAMINES, polyethylenimines from BASF (Ludwigshafen, Germany) under LUPASOL grades (e.g., Lupasol FG, Lupasol G20 waterfree, Lupasol PR 8515, Lupasol WF, Lupasol FC, Lupasol G20, Lupasol G35, Lupasol G100, Lupasol G500, Lupasol HF, Lupasol PS, Lupasol HEO 1, Lupasol PN50, Lupasol PN60, Lupasol PO100 and Lupasol SK). Other commercially available polyethylenimines include EPOMIN P-1000, EPOMIN P-1050, EPOMIN RP18W and EPOMIN PP-061 from NIPPON SHOKUBAI (New York, N.Y.). Polyvinylamines such as those sold by BASF under LUPAMINE grades can also be used. A wide range of polyetheramines may be selected by those skilled in the art. In certain embodiments, the cross-linking agent is hexamethylene diamine, polyetheramine or a mixture thereof.

The structures of specific cross-linking agents are shown in Table 1 below:

TABLE 1

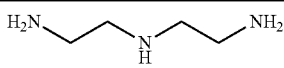

Diethylenetriamine

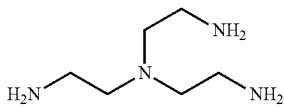

Tris(2-aminoethyl)amine

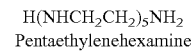

Pentaethylenehexamine

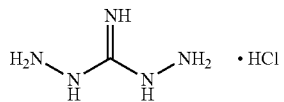

1,3-Diaminoguanidine monohydrochloride

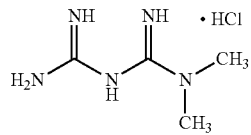

1,1-Dimethylbiguanide hydrochloride

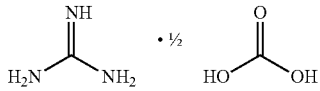

Guanidine carbonate

TABLE 1-continued
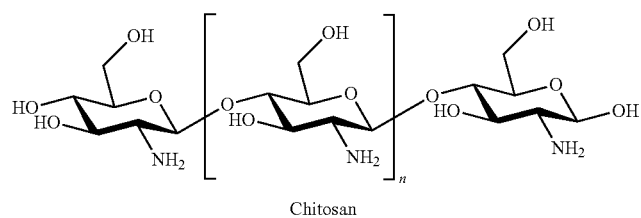
Chitosan
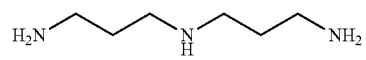
Bis(3-aminopropyl)amine
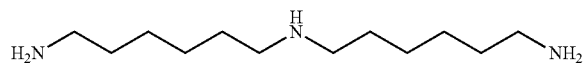
Bis(hexanethylene)triamine
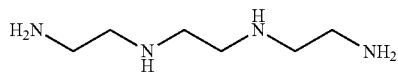
Triethylenetetramine
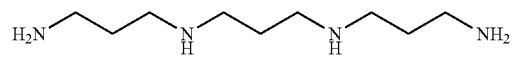
N,N'-Bis(3-aminopropyl)-1,3-propanediamine
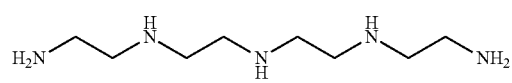
Tetraethylenepentamine
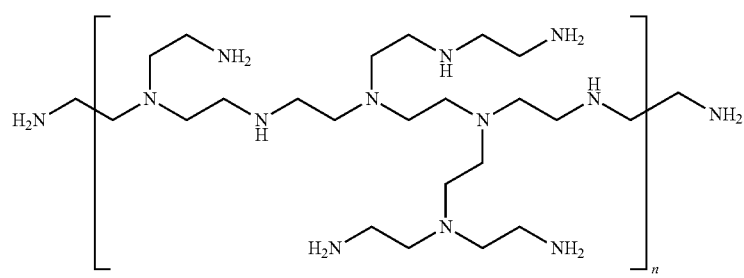
Branched Polyethylenimine

TABLE 1-continued

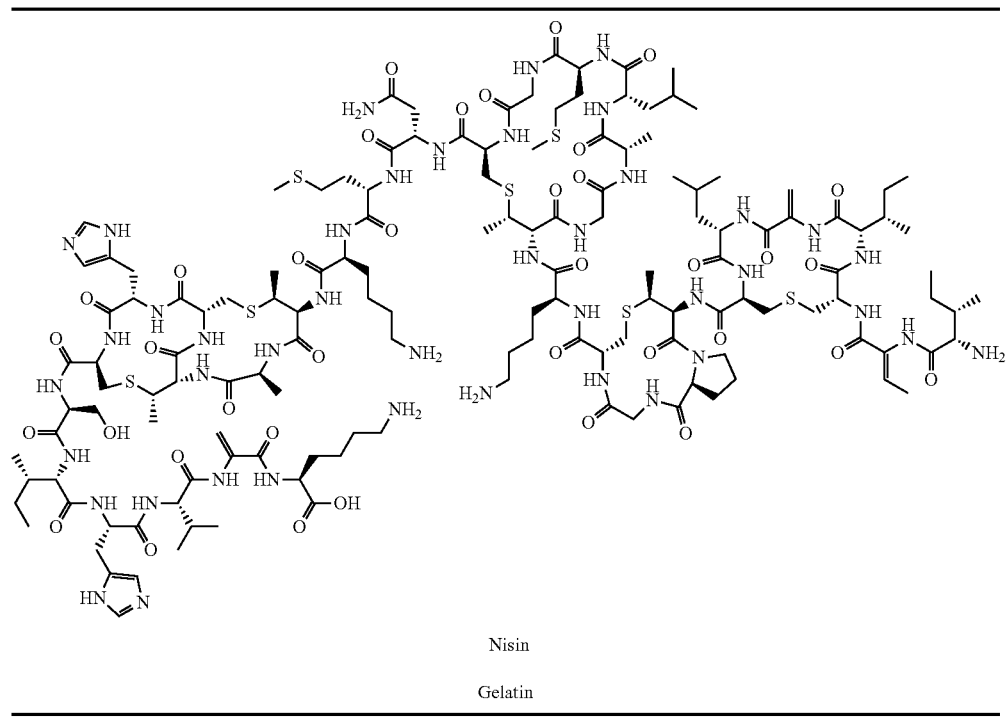

Nisin

Gelatin

Polyols of use in this invention generally have at least two nucleophilic centers (i.e., hydroxyl groups), e.g., ethylene glycol, hexylene glycol, pentaerythritol, glucose, sorbitol, and 2-aminoethanol.

The range of polyamine or polyol concentration can vary from 0.1% to 5% e.g., 0.2% to 3%, 0.2% to 2%, 0.5% to 2%, and 0.5% to 1%) by weight of the polyurea or polyurethane capsule composition.

By adding excess amount of a cross-linking agent, it has been observed that polyurea/polyurethane formation is driven toward completion thereby reducing the amount of residual polyisocyanate. The reaction stoichiometry requires one amine/hydroxyl group per one isocyanate group. By way of illustration, when combining LUPRANATE M20 (having a molecular weight of 360 and isocyanate functionality of 2.7) and hexamethylenediamine (HMDA; having a molecular weight of 116.21 and amine functionality of 2), the stoichiometry of the system indicates that for each gram of HMDA, 2.23 grams of LUPRANATE is needed. The amount of amine will be in excess if more than one gram of HMDA is used per 2.23 grams of LUPRANATE M20. Using a cross-linker in excess, residual isocyanate amounts are reduced by at least 30%. After the capsules are formed, the free cross-link agent (e.g., hexamethylenediamine, amino-2-methyl-1-propanol, lysine, arginine, and histidine) can be present in the capsule slurry at a concentration of 20 ppm to 2%. The amounts of the residual isocyanate and free cross-linking agent can be removed by washing the capsule slurry with water or carbonate/bicarbonate solution (e.g., sodium carbonate, potassium carbonate, sodium bicarbonate, and potassium bicarbonate).

The cross linking agent as used in this invention can be a single compound (e.g., a polyamine) or a mixture of two or more compounds described above (e.g., two polyamines, two polyols, and a mixture of a polyamine and a polyol).

In one embodiment of the invention, the cross linking agent is added to the capsule reaction at a temperature of 0-55° C. (e.g., 10-50° C., 15-45° C., 20-40° C., and 22-35° C.).

Polyvinylpyrrolidone.

Polyvinylpyrrolidone, also known as Polyvidone or Povidone, is a water-soluble polymer. Polyvinylpyrrolidone used in this invention has an molecular weight in the range of 1,000 to 10,000,000.

Polyvinylpyrrolidone products are commonly graded by K values. The K value is an index for correlating relative viscosity with the average degree of polymerization. See Cellulose Chem. 1932, 13, 60. The K value is calculated by the following formula:

$$K=32(1.5 \log \eta_{rel}-1)/(0.15+0.003c)+(300c \log \eta_{rel}+(c+1.5c \log \eta_{rel})^{1/2}/(0.15c+0.003c^2)$$

$\eta_{rel}$: Relative viscosity of aqueous polyvinylpyrrolidone solution to water. c: Content of polyvinylpyrrolidone in an aqueous polyvinylpyrrolidone solution (w/w %).

Polyvinylpyrrolidone used in the formulation has a K value of 12 to 90, e.g., 12, 15, 17, 25, or 30.

There are correlations between K values and molecular weights. For example, polyvinylpyrrolidone K12 has a molecular weight of 2,000 to 4,000, K15 6,000 to 15,000, K17 4,000 to 18,000, K30 40,000 to 62,000, and K90 1,000,000 to 1,500,000. Polyvinylpyrrolidone products from different vendors may have different average molecular weights, which typically fall into the ranges cited above.

Polyvinylpyrrolidone herein refers to a single product or a mixture of several products. For example, it can be polyvinylpyrrolidone K12, K15, K17, K25, K30, K60, K90, or a mixture thereof. The amount of polyvinylpyrrolidone is 2-50%, 5-30%, or 10-25% by weight of the formulation.

This compound has a structure showing below:

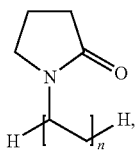

wherein n is 8-10,000.

Alkylnaphthalenesulfonate Formaldehyde Condensates.

Commercially available products include MORWET D-425, which is a sodium salt of naphthalene sulfonate condensate by Akzo Nobel, Fort Worth, Tex. A typical structure is shown below:

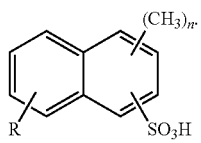

Chain Termination Agent.

Polymerization reactions for forming polyurea/polyurethane capsule wall can be terminated by adding a chain termination agent, e.g., a monofunctional amine or alcohol. Further, a chain termination agent also reacts with isocyanate groups on the surface of the capsules, thus reduced/eliminated isocyanate groups. Examples of a chain termination agent include $C_1$-$C_{20}$ primary and secondary amines, $C_1$-$C_{20}$ alcohols, $C_1$-$C_{20}$ thiols, and any combination thereof.

Capsule Formation Aid.

Some capsules useful in the compositions of this invention are prepared in the presence of a capsule formation aid, which can be a surfactant or dispersant. Not to be bound by any theory, capsule formation aids improve the performance of the capsule system. Performance is measured by the intensity of the fragrance release during the pre-rub and post-rub phases. The pre-rub phase is the phase when the capsules have been deposited on the cloth, e.g., after a fabric softener containing capsules has been used during the wash cycle. The post-rub phase is after the capsules have been deposited and the capsules are broken by friction or other similar mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinyl alcohols (PVA), sodium salt of naphthalene sulfonate condensate, carboxymethyl cellulose (CMC), fatty acid esters of polyoxyethylenated sorbitol, sodium dodecylsulfate, and any combination thereof. In general, the range of surfactant concentration in the capsule composition varies from 0.1 to 5% (e.g., 0.5% to 4%, 0.2% to 2%, and 1% to 2%).

Commercially available surfactants include, but are not limited to, partially hydrolyzed polyvinyl alcohols such as MOWIOLs, e.g., MOWIOL 3-83 (Air Products; a degree of hydrolysis of 83% and an average molecular weight of 14,000); ethylene oxide-propylene oxide block copolymers or poloxamers such as PLURONIC, SYNPERONIC or PLURACARE materials (BASF); sulfonated polystyrenes such as FLEXAN II (sodium polystyrene sulfonate commercially available from Akzo Nobel); ethylene-maleic anhydride polymers such as ZEMAC series from Vertellus Specialties Inc. (e.g., ZeMac E400, an alternating copolymer of ethylene and maleic anhydride having a average molecular weight of 400,000); and Polyquaternium series such as Polyquaternium 11 ("PQ11;" a copolymer of vinyl pyrrolidone and quaternized dimethylaminoethyl methacrylate; sold by BASF as LUVIQUAT PQ11 AT 1).

Processing aids can include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly (vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly (acrylic acid-co-maleic acid)copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms.

The capsule formation aid may also be used in combination with CMC and/or a surfactant during processing to facilitate capsule formation. Examples of surfactants that can be used in combination with the capsule formation aid include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. The amount of surfactant present in the capsule slurry can vary depending on the surfactant used. In some embodiments the amount of surfactant is in the range of 0.05% to 0.2% by weight of the capsule compositions, in particular when CTAC is employed. In another embodiment, the amount of surfactant is in the range of 1% to 3%.

When combined with CMC, a lighter color PVA is preferred. According to the invention, the CMC polymer may be represented by the following structure:

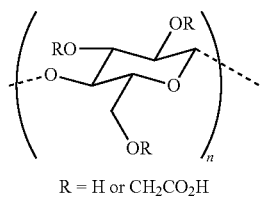

R = H or $CH_2CO_2H$

In certain embodiments, the CMC polymer has a molecular weight range between 90,000 Daltons to 1,500,000 Daltons, preferably between 250,000 Daltons to 750,000 Daltons and more preferably between 400,000 Daltons to 750,000 Daltons. The CMC polymer has a degree of substitution between 0.1 to 3, preferably between 0.65 to 1.4, and more preferably between 0.8 to 1.

The carboxymethyl cellulose polymer is present in the capsule slurry at a level from 0.1 to 2% and preferably from 0.3 to 0.7%.

In some embodiments, capsules formed in presence of a capsule aid may unexpectedly provide a perceived fragrance intensity increase of greater than 15%, and preferably an increase of greater than 25% as compared to capsules formed without a capsule formation aid.

Other Encapsulation Systems:

The microcapsule composition of this invention can contain one or more additional microcapsules that are different from each other, namely, capsules having one or more different properties, e.g., size, wall thickness, wall polymer, degree of crosslinking, and etc. These capsule properties can be manipulated by, e.g., varying the wall-forming material, the amount of capsule wall-forming material in the emulsions, curing temperature/time, and/or droplet size, incorporating benefit agents that affect the wall properties, modulating the shear rate after each benefit agent addition, choosing the type of cross-linkers used, and any combination thereof.

Encapsulation of active material such as fragrances is known in the art, see for example U.S. Pat. Nos. 2,800,457, 3,870,542, 3,516,941, 3,415,758, 3,041,288, 5,112,688, 6,329,057, and 6,261,483. Preferred encapsulating polymers include those formed from, acrylates, acrylamide, acrylate-co-acrylamide, melamine-formaldehyde or urea-formaldehyde condensates, as well as similar types of aminoplasts. Other wall forming materials include, polysiloxanes, polyamide, polyimide, polyvinyl alcohol, polyanhydride, polyolefin, polysulfone, polysaccaharide, protein, polylactide (PLA), polyglycolide (PGA), polyorthoester, polyphosphazene, silicone, lipid, modified cellulose, gums, polystyrene, and polyesters or combinations of these materials. Other polymeric materials that are functional are ethylene maleic anyhydride copolymer, styrene maleic anhydride copolymer, ethylene vinyl acetate copolymer, and lactide glycolide copolymer. Bio-polymers that are derived from alginate, chitosan, collegen, dextran, gelatin, and starch can also be used as the encapsulating materials. Additionally, microcapsules can be made via the simple or complex coacervation of gelatin.

In addition to microcapsules, the microcapsule composition of this invention can contain one or more additional other delivery compositions such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof.

I. Polymer Matrix Delivery System i) Melt Extruded Flavor/Fragrance (1) High molecular weight carbohydrate including starches, modified starches.

(2) Low molecular weight carbohydrates of a low molecular weight carbohydrate or polyol, wherein said low molecular weight carbohydrate or polyol is selected from the group consisting of glucose, sucrose, maltose, lactose, corn syrup solid, erythritol, lactitol, mannitol, sorbitol, maltitol, isomalt, xylitol, trehalose, hydrogenated corn syrup, hydrogenated glucose syrup, hydrogenated maltose syrup, hydrogenated lactose syrup, starch hydrolysate, and a mixture thereof, and wherein said glassy matrix has a glass transition temperature of greater than room temperature.

(3) Polymers (various polymers are useful in the practice of our invention. Specific examples of polymers useful in the practice of our invention are as follows: DYLAN.sup.® of low density polyethylene (DYLAN.sup® is a trademark owned by the Atlantic Richfield Company of Los Angeles, Calif. DYLITE.sup.® of expandable polystyrene compositions. DYLITE.sup.® is a trademark of the Atlantic Richfield Company of Los Angeles, Calif. SUPER DYLAN.sup.® of high density polyethylene. SUPER DYLAN.sup.® a trademark of the Atlantic Richfield Company of Los Angeles, Calif.

Blended polyethylene and carbon black as specifically taught in U.S. Pat. No. 4,369,267 issued on Jan. 18, 1983, the specification for which is incorporated by reference herein.

Polystyrene as disclosed in U.S. Pat. No. 4,369,227 issued on Jan. 18, 1983, the specification for which is incorporated by reference herein. Polyene/alpha-olefin copolymers as exemplified and disclosed in U.S. Pat. No. 4,369,291, the specification for which is incorporated by reference herein. Poly-alpha-olefins as exemplified in Canadian Letters Pat. No. 1,137,069 issued on Dec. 7, 1982, the specification for which is incorporated by reference herein. Polymeric compositions as disclosed in Canadian Letters Pat. No. 1,137,068 issued on Dec. 7, 1982, the specification for which is incorporated by reference herein. Poly-alpha-olefins disclosed in Canadian Letters Pat. No. 1,137,067, the specification for which is incorporated by reference herein.

Polyolefins described in Canadian Letters Pat. No. 1,137,066, the specification for which is incorporated by reference herein. Polyethylene oxides as disclosed in Canadian Letters Pat. No. 1,137,065 issued on Dec. 7, 1982, the specification for which is incorporated by reference herein.

Olefin polymers and co-polymers as disclosed in Canadian Letters Pat. No. 1,139,737, the disclosure of which is incorporated by reference herein. Canadian Pat. No. 1,139,737 was issued on Jan. 18, 1983. Polyolefins disclosed in Canadian Letters Pat. No. 1,139,738, the specification for which is incorporated by reference herein. Canadian Pat. No. 1,139,738 was issued on Jan. 18, 1983. Chlorinated PVC as disclosed in Polymer 1982, 23 (7, Suppl.), 1051-6 abstracted at Chem. Abstracts 97:145570y, 1982.

Polyepsilon caprolactone co-polymers made by means of alcohol initiated polymerization as disclosed in J. Polym. Sci. Polym. Chem. Ed. 1982, 20(2), pages 319-26, abstracted at Chem. Abstracts, Volume 96: 123625x, 1982. Styrene acrylonitrile co-polymers as disclosed in Diss. Abstracts, Int. B, 1982, 42(8), 3346 and abstracted at Chem. Abstracts 96:143750n (1982). Co-polymers of epsilon caprolactone with 1,4-butane diol as disclosed at Kauch. Rezine, 1982, (2), 8-9, abstracted at Chem. Abstracts, volume 96:182506 g (1982). Polyesters as disclosed in U.S. Pat. No. 4,326,010, the specification for which is incorporated by reference herein.

Chlorinated polyethylene as disclosed by Belorgey, et. al. J. Polym. Sci. Polym. Phys. Ed. 1982, 20(2), 191-203. Plasticized polyepsilon caprolactone co-polymers containing dimethyl phthalate plasticizers as set forth in Japanese Pat. No. J81/147844, abstracted at Chem. Abstracts, Volume 96:69984y (1982), the specification for which is incorporated by reference herein. Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein. Polyurethane polymers having lactone backbones as disclosed in U.S. Pat. No. 4,156,067 issued on May 22, 1979, the disclosure of which is incorporated by reference herein. Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein. Resins having polyurethane backbones as disclosed in U.S. Pat. No. 3,975,350 issued on Aug. 17, 1976, the disclosure of which is incorporated by reference herein.

(4) Suitable plasticizers include water; glycerol; propylene glycol; aqueous solutions of glycerol, propylene glycol, monosaccharides, and disaccharides; and invert and high fructose corn syrups.

(5) Emulsifier. surface-active agent, i.e. an emulsifier can be added to the dry blend, or preferably added to the liquid flavor mix which is ultimately injected into the metering zone of the extruder. These emulsifiers can be from the class of distilled monoglycerides, mono- and diglyceride blends, propyleneglycol monoglycerides, lecithin, modified lecithins, acetylated monoglycerides, lactylated monoglycerides, lactylated propyleneglycol monoglycerides, sorbitan esters, sorbitan-polyoxyethylene [20] monoglycerides, polyglycerol esters, DATEM's (diacetyltartarate esters of monoglycerides), succinylated esters of monoglycerides and polyoxyethylenepropylene copolymers and mixtures thereof. Most preferred surfactants are the sorbitan-polyoxyethylene [20] monoglycerides, lecithins, and polyglycerol esters.

ii) Spray Dry Encapsulation (1) The matrix is comprised of one or more of the following materials: sugars such as glucose, fructose, lactose, galactose, ribose, xylose, sucrose, maltose; polyols such as glycerin and propylene glycol; corn syrups, maltodextrin, fats, silicone dioxide, polyhydric alcohols, corn syrup solids, starches, modified starches, emulsifiers and food acids. The level of maltodextrin used in the matrix, comprises from 25 to 98 weight percent, preferably from 35 to 75 weight percent.

(2) Core modifiers: flavors and fragrance may also be combined with a variety of solvents which serve to increase the compatibility of the various materials, increase the overall hydrophobicity of the blend, influence the vapor pressure of the materials, or serve to structure the blend. Solvents performing these functions are well known in the art and include mineral oils, triglyceride oils, silicone oils, fats, waxes, fatty alcohols, diisodecyl adipate, and diethyl phthalate among others.

(3) emulsifiers including monoglycerides of fatty acids, distilled succinylated monoglycerides of fatty acids, sorbitan fatty acid esters; distilled acetylated monoglycerides of fatty acids, monoglycerides of fatty acids.

II. Single Wall Capsules i) Aminoplast: A representative process used for aminoplast encapsulation is disclosed in U.S. Pat. No. 3,516,941 though it is recognized that many variations with regard to material and process steps are possible. A representative process used for gelatin encapsulation is disclosed in U.S. Pat. No. 2,800,457 though it is recognized that many variations with regard to material and process steps are possible. Both of these processes are discussed in the context of fragrance encapsulation for use in consumer products in U.S. Pat. Nos. 4,145,184 and 5,112,688 respectively. Polymers systems are well know in the art and non-limiting examples of these include aminoplast capsules and encapsulated particles as disclosed in GB GB2006709 A; the production of microcapsules having walls comprising styrene-maleic anhydride reacted with melamine-formaldehyde precondensates as disclosed in U.S. Pat. No. 4,396,670; an acrylic acid-acrylamide copolymer, cross linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amidoaldehyde resin in-situ polymerized capsules disclosed in EP 0 158 449 A1; etherified urea-formaldehyde polymer as disclosed in U.S. Pat. No. 5,204,185; melamine-formaldehyde microcapsules U.S. Pat. No. 4,525,520; cross linked oil-soluble melamine-formaldehyde precondensate U.S. Pat. No. 5,011,634; capsule wall material formed from a complex of cationic and anionic melamine-formaldehyde precondensates that are then cross linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; capsules composed of polymer or copolymer of styrene sulfonic acid in acid of salt form, and capsules cross linked with melamine-formaldehyde as disclosed in U.S. Pat. No. 4,001,140. Urea-formaldehyde and melamine-formaldehyde pre-condensate microcapsule shell wall precursors are prepared by means of reacting urea or melamine with formaldehyde where the mole ratio of melamine or urea to formaldehyde is in the range of from 10:1 to 1:6, preferably from 1:2 to 1:5. For purposes of practicing our invention, the resulting material has a molecular weight in the range of from 156 to 3000. The resulting material may be used ' as-is' as a cross-linking agent for the aforementioned substituted or un-substituted acrylic acid polymer or copolymer or it may be further reacted with a C1-C6 alkanol, e.g. methanol, ethanol, 2-propanol, 3-propanol, 1-butanol, 1-pentanol or 1-hexanol, thereby forming a partial ether where the mole ratio of melamine or urea:formaldehyde:alkanol is in the range of 1:(0.1-6):(0.1-6). The resulting ether moiety-containing product may by used ' as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. Nos. 3,516,846, 6,261,483, and Lee et al. J. Microencapsulation, 2002, Vol. 19, No. 5, pp 559-569, "Microencapsulation of fragrant oil via in situ polymerization: effects of pH and melamine-formaldehyde molar ratio". Examples of urea-formaldehyde pre-condensates useful in the practice of our invention are URAC 180 and URAC 186, trademarks of Cytec Technology Corp. of Wilmington, Del. 19801, U.S.A. Examples of melamine-formaldehyde pre-condensates useful in the practice are CYMEL U-60, CYMEL U-64 and CYMEL U-65, trademarks of Cytec Technology Corp. of Wilmington, Del. 19801, U.S.A. It is preferable to use as the precondensate for cross-linking the substituted or un-substituted acrylic acid polymer or co-polymer. In practicing our invention, the range of mole ratios of urea-formaldehyde precondensate or melamine-formaldehyde pre-condensate: substituted or un-substituted acrylic acid polymer or co-polymer is in the range of from 9:1 to 1:9, preferably from 5:1 to 1:5 and most preferably from 2:1 to 1:2. In another embodiment of the invention, microcapsules with polymer(s) comprising primary and/or secondary amine reactive groups or mixtures thereof and crosslinkers as disclosed in commonly assigned U.S. patent application Ser. No. 11/123,898. The amine polymers can possess primary and/or secondary amine functionalities and can be of either natural or synthetic origin. Amine containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the Lupamin series of polyvinyl formamides (available from BASF). The molecular weights of these materials can range from 10,000 to 1,000,000.

(1) Dispersant (2) Scavengers: Typical formaldehyde scavengers comprise compounds capable of binding free formaldehyde in aqueous media, such as sodium sulfite, melamine, glycine, and carbohydrazine. However, when the microcapsules are aimed to be used in products having low pH, such as fabric care conditioners, formaldehyde scavengers are preferably selected from beta diketones, such as beta-ketoesters, or from 1,3-diols, such as propylene glycol. Preferred beta-ketoesters comprise alkyl-malonates, alkyl aceto acetates and polyvinyl alcohol aceto acetates.

(3) Processing Aids ii) Hydrogel (1) Monomers: Preferred bi- or polyfunctional vinyl monomers include by way of illustration and not limitation, allyl methacrylate; triethylene glycol dimethacrylate; ethylene glycol dimethacrylate, diethylene glycol dimethacrylate, aliphatic or aromatic urethane diacrylates, difunctional urethane acrylates, ethoxylated aliphatic difunctional urethane methacrylates, aliphatic or aromatic urethane dimethacrylates, epoxy acrylates, epoxymethacrylates; tetraethylene glycol dimethacrylate; polyethylene glycol dimethacrylate; 1,3 butylene glycol diacrylate; 1,4-butanediol dimethacrylate; 1,4-butaneidiol diacrylate; diethylene glycol diacrylate; 1,6 hexanediol diacrylate; 1,6 hexanediol dimethacrylate; neopentyl glycol diacrylate; polyethylene glycol diacrylate; tetraethylene glycol diacrylate; triethylene glycol diacrylate; 1,3 butylene glycol dimethacrylate; tripropylene glycol diacrylate; ethoxylated bisphenol diacrylate; ethoxylated bisphenol dimethylacrylate; dipropylene glycol diacrylate; alkoxylated hexanediol diacrylate; alkoxylated cyclohexane dimethanol diacrylate; propoxylated neopentyl glycol diacrylate, trimethylolpropane trimethacrylate; trimethylolpropane triacrylate, pentaerythritol triacrylate, ethoxylated trimethylolpropane triacrylate, propoxylated trimethylolpropane triacrylate, propoxylated glyceryl triacrylate, ditrimethyloipropane tetraacrylate, dipentaerythritol pentaacrylate, ethoxylated pentaerythritol tetraacrylate.

(2) Initiators including but not limited to: AIBN, sodium persulfate, benzoyl peroxide.

(3) Emulsifiers: Anionic emulsifiers include by way of illustrating and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from 0.1 to 40 percent by weight of all constitutents, more preferably from 0.5 to 10 percent, more preferably 0.5 to 5 percent by weight.

iii) Sol-Gel

Sol-gel precursors, i.e. starting compounds capable of forming gels, suitable for the purposes of the invention are known per se to the expert. Sol-gel precursors usable in accordance with the invention are, for example, compounds, which are capable of forming gels, such as silicon, boron, aluminum, titanium, zinc, zirconium and vanadium. The precursors can also include metal alkoxides and bdiketonates Sol-gel precursors suitable for the purposes of the invention are selected in particular from the group of di-, triand/or tetrafunctional silicic acid, boric acid and alumoesters, more particularly alkoxysilanes (alkyl orthosilicates), and precursors thereof. One example of sol-gel precursors suitable for the purposes of the invention are alkoxysilanes corresponding to the following general formula: $(R1O)(R2O)M(X)(X')$ wherein X is equal to hydrogen, or —OR3, and X' is equal to hydrogen, or —OR4 and R1, R2, R3 and R4 independently represent an organic group, more particularly a linear or branched alkyl group, preferably a C1-12 alkyl. M can be equal to Si, Ti, and Zr.

iv) Coacervate Capsules.

(1) Proteins useful in coacervation processes include albumins, vegetable globulins and gelatines. The gelatine may be fish, pork, beef, and/or poultry gelatine, for example. According to a preferred embodiment, the protein is fish, beef or poultry gelatine. According to a more preferred embodiment, the protein is warm water fish gelatine.

(2) Typical non-protein polymers useful in complex coacervation methods include, in particular, negatively charged polymers. For example, they may be selected from gum arabic, xanthan, agar, alginate salts, cellulose derivatives, for example carboxymethyl cellulose, pectinate salts, carrageenan, polyacrylic and methacrylic acid, and/or mixtures thereof. Further suitable non-proteins can be derived from the literature, for example from WO 2004/022221, page 4, lines 27-29.

(3) A cross-linking agent is typically used to harden the coating layer. Suitable cross-linking agents include formaldehyde, acetaldehyde, glutaraldehyde, glyoxal, chrome alum, or transglutaminase. Preferably, transglutaminase is used at 10-100, preferably 30-60 activity units per gram of gelatine. This enzyme is well described and commercially obtainable.

III. Cyclodextrin Delivery System

This technology approach uses a cyclic oligosaccharide or cyclodextrin to improve the delivery of perfume. Typically, a perfume and cyclodextrin (CD) complex is formed. Such complexes may be preformed, formed in-situ, or formed on or in the situs. See, e.g., WO 2013/109798 A2 and US 2011/0308556 A1.

IV. Pro-Perfume i) Michael Addition reaction products of a primary/secondary amine with an unsaturated ester, acid or nitrile perfume compound such those described in U.S. Pat. No. 6,858,575.

ii) Reaction product between a primary/secondary amine compound/polymer and a ketone or aldehyde perfume compound such as those described in WO 2001/051599 A1 and WO 2002/092746 A1.

iii) other nonlimiting examples include aromatic or non-aromatic imines (Schiff bases), oxazolidines, beta-keto esters, orthoesters, compounds comprising one or more beta-oxy or beta-thio carbonyl moieties capable of releasing a perfume (e.g., an alpha, beta-unsaturated ketone, aldehyde or carboxylic ester). The typical trigger for perfume release is exposure to water; although other triggers may include enzymes, heat, light, pH change, autoxidation, a shift of equilibrium, change in concentration or ionic strength and others. Suitable pro-perfumes and methods of making same can be found in U.S. Pat. Nos. 8,912,350 B2, 7,018,978 B2; 6,987,084 B2; 6,956,013 B2; 6,861,402 B1; 6,544,945 B1; 6,093,691; 6,277,796 B1; 6,165,953; 6,316,397 B1; 6,437,150 B1; 6,479,682 B1; 6,096,918; 6,218,355 B1; 6,133,228; 6,147,037; 7,109,153 B2; 7,071,151 B2; 6,987,084 B2; 6,916,769 B2; 6,610,646 B2 and 5,958,870, as well as can be found in US 2005/0003980 A1 and US 2006/0223726 A1.

Additional Polymers.

In addition to the polyisocyanate, cross-linking agent, the encapsulating polymer can also include one or more additional polymers. Additional polymers that can be added to the wall at the formation of the capsules include, e.g., polyamines (polyethylenimine, poly vinyl amines, etc.), polyacrylates and polyquaterniums. In certain embodiments, the additional polymers may be selected from, but is not limited to, amphoteric and cationic polymers having a molecular weight in the range of from 1,000 to 1,000,000, preferably from 10,000 to 500,000, and more preferred between 100,000 to 200,000. Not to be bound by any theory, these additional polymer change the surface property of capsules, improve the stability of the capsules for storage, and/or increase affinity of capsules to treated surface area (e.g., as deposition aids).

Examples of amphoteric and cationic polymers include, but not limited to, polyquaternium and polyvinylamine and its copolymers with vinylformamide and mixtures thereof. Polyquaternium includes polyquaternium-6 (poly(diallyldimethyl-ammonium chloride), commercially available from Lubrizol as MERQUAT 100), polyquaternium-22 (commercially available from Lubrizol as MERQUAT 280), polyquaternium-39 (commercially available from Lubrizol as MERQUAT 3330), polyquaternium-47 (a terpolymer of acrylic acid, methacrylamidopropyl trimethylammonium chloride, and methyl acrylate, commercially available as MERQUAT 2001), and polyquaternium-53 (copolymer of acrylic acid, acrylamide, methacrylamidopropyltrimonium chloride, commercially available as MERQUAT 2003PR). Polyvinylamines are polymers which are prepared by acidic or alkaline hydrolysis of poly(N-vinylformamides), as described, e.g., by Gu, et al. ((2002) *J. Appl. Pol. Sci.* 86:3412-3419). The corresponding products are produced in various molecular weights by BASF AG under the trade name "LUPAMIN". These products are used on a large scale, for example, as paper chemicals, in the personal care sector, as super-absorbents or dispersants. The LUPAMIN commercial products still contain the salts formed from the hydrolysis. For the application sector described, the modification of waveguide surfaces, both the salt-containing and the desalinified form can be used. The desalinification can be effected, for example, by ultrafiltration. In a preferred embodiment the polyvinylamine is LUPAMIN 9095 (polyvinylamine, average molecular weight 340,000 g/mol) commercially available from BASF. Polyethyleneimine are commercially available, e.g., Lupasol G20 and Lupasol SK, both by BASF. In another preferred embodiment, the additional amine is a mixture of polyvinylamine and alginate.

In some embodiments, the encapsulating polymer contains from 0.01 to 20 weight percent of the additional polymer, on a solid basis. In other embodiments, the encapsulating polymer contains from 0.1 to 10 weight percent of the additional polymer, on a solid basis. In particular embodiments, the additional polymer is polyquaternium-6 and is present, on a solid basis, in the range of 0.25 to 10 weight percent. In a further embodiment, the polymer is a mixture of polyquaternium-6 and a polyvinyl amine, specifically LUPAMIN 9095, wherein the polyquaternium-6 may be present, on a solid basis, in the range of preferably 0.5 to 5 weight percent and the polyvinylamine present, on a solid basis, from 0.25 to 10 weight percent. In still a further embodiment, the additional polymer is a mixture of polyquaternium-6 and polyvinylamine wherein the polyquaternium-6 is present, on a solid basis, in the range of preferably 0.5 to 5 weight percent and the polyvinylamine is present, on a solid basis, in the range of preferably 0.5 to 8 weight percent. In yet another embodiment, the additional polymer is a mixture of polyquaternium-6 and polyvinylamine wherein the polyquaternium-6 is present, on a solid basis, at a level of 1.5 weight percent and the polyvinylamine is present, on a solid basis, 1 weight percent.

According to certain other embodiments of the invention, the additional polymer is added at between 35° C. and 55° C.

Catalysts.

Catalysts suitable for use in the invention are metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate and dibutyltin dilaurate.

Core/Active Materials.

The core of the capsules of the invention can include one or more active materials including, but not limited to, flavors, fragrance ingredients such as fragrance oils, taste masking agents, taste sensates, malodor counteractants (i.e., malodor counteractive agents and malodor control agents), vitamins, dyes, colorants, pigments, anti-inflammatory agents, anesthetics, analgesics, anti-fungal agents, antibiotics, anti-viral agents, anti-parasitic agents, anti-infectious/anti-acne agents, dermatological active ingredients, enzymes and co-enzymes, skin whitening agents, anti-histamines, chemotherapeutic agents, insect repellents, sunscreen actives, core modifiers, and sacrificial core ingredients.

Perfumes that can be included in the capsules of this invention include fragrances containing:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, menthan-8-ol, menthan-1-ol, menthan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha, 3,3-trimethylcyclohexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert.-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetra-methylcyclohexanone, 4-tert.-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert.-butyl-(2,4-dimethyl-3-cyclohexen-1-yl)ketone;

xv) esters of cyclic alcohols, such as, for example, 2-tert.-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)-propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-iso-propylphenyl)propanal, 2-methyl-3-(4-tert.-butylphenyl)propanal, 3-(4-tert.-butylphenyl) propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert.-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert.-butyl-1,1-dimethyl-4-indanyl methyl ketone, 1-[2,3-dihydro-1,1,2,6-tetramethyl-3-(1-methylethyl)-1H-5-indenyl]ethanone, 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methy-N-methylanthranilate, Schiff's bases of methyl anthranilate with 7-hydroxy-3,7-dimethyloctanal, 2-methyl-3-(4-tert.-butylphenyl)-propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, Litsea cubeba oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

Flavors that can be included in the capsules of this invention may include, but are not limited to, acetaldehyde, dimethyl sulfide, ethyl acetate, ethyl propionate, methyl butyrate, and ethyl butyrate. Flavors containing volatile aldehydes or esters include, e.g., cinnamyl acetate, cinnamaldehyde, citral, diethylacetal, dihydrocarvyl acetate, eugenyl formate, and p-methylanisole. Further examples of volatile compounds that may be present in the instant flavor oils include acetaldehyde (apple); benzaldehyde (cherry, almond); cinnamic aldehyde (cinnamon); citral, i.e., alpha citral (lemon, lime); neral, i.e., beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., melonal (melon); 2-6-dimethyloctanal (green fruit); and 2-dodecenal (citrus, mandarin); cherry; or grape and mixtures thereof. The composition may also contain taste modulators and artificial sweeteners. As used herein, flavor is understood to include spice oleoresins derived from allspice, basil, capsicum, cinnamon, cloves, cumin, dill, garlic, marjoram, nutmeg, paprika, black pepper, rosemary, and turmeric, essential oils, anise oil, caraway oil, clove oil, eucalyptus oil, fennel oil, garlic oil, ginger oil, peppermint oil, onion oil, pepper oil, rosemary oil, spearmint oil, citrus oil, orange oil, lemon oil, bitter orange oil, tangerine oil, alliaceous flavors, garlic, leek, chive, and onion, botanical extracts, arnica flower extract, chamomile flower extract, hops extract, marigold extract, botanical flavor extracts, blackberry, chicory root, cocoa, coffee, kola, licorice root, rose hips, sarsaparilla root, sassafras bark, tamarind and vanilla extracts, protein hydrolysates, hydrolyzed vegetable proteins, meat protein hydrolyzes, milk protein hydrolyzates and compounded flavors both natural and artificial including those disclosed in S. Heath, Source Book of Flavors, Avi Publishing Co., Westport Conn., 1981, pages 149-277. Specific preferred flavor adjuvants include, but are not limited to, the following: anise oil; ethyl-2-methyl butyrate; vanillin; cis-3-heptenol; cis-3-hexenol; trans-2-heptenal; butyl valerate; 2,3-diethyl pyrazine; methylcyclo-pentenolone; benzaldehyde; valerian oil; 3,4-dimethoxyphenol; amyl acetate; amyl cinnamate, y-butyryl lactone; furfural; trimethyl pyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; g-hexenyl lactone; 2,4-decadienal; 2,4-heptadienal; methyl thiazole alcohol (4-methyl-5-b-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; b-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethyl pyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolane; and 4-methyl-2-(methylthiomethyl)-1,3-dithiolane. These and other flavor ingredients are provided in U.S. Pat. Nos. 6,110,520 and 6,333,180.

Taste masking agents are substances for masking one or more unpleasant taste sensations, in particular a bitter, astringent and/or metallic taste sensation or aftertaste, which substances can be a constituent of the products according to the invention. Examples include lactisol [2O-(4-methoxyphenyl) lactic acid] (cf U.S. Pat. No. 5,045,336), 2,4-dihydroxybenzoic acid potassium salt (cf U.S. Pat. No. 5,643,941), ginger extracts (cf GB 2,380,936), neohesperidine dihydrochalcone (cf. Manufacturing Chemist 2000, July issue, p. 16-17), specific flavones (2-phenylchrom-2-en-4-ones) (cf U.S. Pat. No. 5,580,545), specific nucleotides, for example cytidine-5'-monophosphates (CMP) (cf US 2002/0177576), specific sodium salts, such as sodium chloride, sodium citrate, sodium acetate and sodium lactate (cf Nature, 1997, Vol. 387, p. 563), a lipoprotein of .beta.-lactoglobulin and phosphatidic acid (cf EPA 635 218), neodiosmine [5,7-dihydroxy-2-(4-methoxy-3-hydroxyphenyl)-7-O-neohesperidosyl-chrom-2-en-4-one] (cf U.S. Pat. No. 4,154,862), preferably hydroxyflavanones according to EP 1 258 200, in turn preferred in this respect 2-(4-hydroxyphenyl)-5,7-dihydroxychroman-4-one (naringenin), 2-(3,4-dihydroxyphenyl)-5,7-dihydroxychroman-4-one (eriodictyol), 2-(3,4-dihydroxyphenyl)-5-hydroxy-7-methoxychroman-4-one (eriodictyol-7-methylether), 2-(3,4-dihydroxyphenyl)-7-hydroxy-5-methoxychroman-4-one (eriodictyol-5-methylether) and 2-(4-hydroxy-3-methoxyphenyl)-5,7-dihydroxychroman-4-one (homoeriodictyol), the (2S)- or (2R)-enantiomers thereof or mixtures thereof as well as the mono- or polyvalent phenolate salts thereof with Na.sup.+, K.sup.+, NH.sup.4+, Ca.sup.2+, Mg.sup.2+ or Al.sup.3+ as counter cations or .gamma.-aminobutyric acid (4-aminobutyric acid, as the neutral form ("inner salt") or in the carboxylate or ammonium form) according to WO 2005/096841.

Taste sensates include hot tasting, salivation-inducing substances, substances causing a warmth or tingling feeling, and cooling active ingredients.

Examples of hot tasting and/or salivation-inducing substances and/or substances which cause a feeling of warmth and/or a tingling feeling on the skin or on the mucous membranes and which can be a constituent of the products according to the invention are: capsaicin, dihydrocapsaicin, gingerol, paradol, shogaol, piperine, carboxylic acid-N-vanillylamides, in particular nonanoic acid-N-vanillylamide, pellitorin or spilanthol, 2-nonanoic acid amides, in particular 2-nonanoic acid-N-isobutylamide, 2-nonanoic acid-N-4-hydroxy-3-methoxyphenylamide, alkyl ethers of 4-hydroxy-3-methoxybenzyl alcohol, in particular 4-hydroxy-3-methoxybenzyl-n-butylether, alkyl ethers of 4-acyloxy-3-methoxybenzyl alcohol, in particular 4-acetyloxy-3-methoxybenzyl-n-butylether and 4-acetyloxy-3-methoxybenzyl-n-hexylether, alkyl ethers of 3-hydroxy-4-methoxybenzyl alcohol, alkyl ethers of 3,4- dimethoxybenzyl alcohol, alkyl ethers of 3-ethoxy-4-hydroxybenzyl alcohol, alkyl ethers of 3,4-methylene dioxybenzyl alcohol, (4-hydroxy-3-methoxyphenyl)acetic acid amides, in particular (4-hydroxy-3-methoxyphenyl) acetic acid-N-n-octylamide, vanillomandelic acid alkylamides, ferulic acid-phenethylamides, nicotinaldehyde, methylnicotinate, propylnicotinate, 2-butoxyethylnicotinate, benzylnicotinate, 1-acetoxychavicol, polygodial and isodrimeninol, further preferred cis- and/or trans-pellitorin according to WO 2004/000787 or WO 2004/043906, alkenecarboxylic acid-N-alkylamides according to WO 2005/044778, mandelic acid alkylamides according to WO 03/106404 or alkyloxyalkanoic acid amides according to WO 2006/003210. Examples of preferred hot tasting natural extracts and/or natural extracts which cause a feeling of warmth and/or a tingling feeling on the skin or on the mucous membranes and which can be a constituent of the products according to the invention are: extracts of paprika, extracts of pepper (for example capsicum extract), extracts of chili pepper, extracts of ginger roots, extracts of *Aframomum melgueta*, extracts of *Spilanthes-acmella*, extracts of *Kaempferia galangal* or extracts of *Alpinia galanga*.

Suitable cooling active ingredients include the following: 1-menthol, d-menthol, racemic menthol, menthone glycerol acetal (trade name: Frescolat® MGA), menthyl lactate (trade name: Frescolat® ML, menthyl lactate preferably being 1-menthyl lactate, in particular 1-menthyl-1-lactate), substituted menthyl-3-carboxamides (for example menthyl-3-carboxylic acid-N-ethylamide), 2-isopropyl-N-2,3-trimethyl-butanamide, substituted cyclohexane carboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (for example menthyl-3-hydroxybutyrate), monomenthyl succinate, 2-mercaptocyclodecanone, menthyl-2-pyrrolidin-5-onecarboxylate, 2,3-dihydroxy-p-menthane, 3,3,5-trimethylcyclohexanone glycerol ketal, 3-menthyl-3,6-di- and -trioxaalkanoates, 3-menthyl methoxyacetate and icilin. Cooling active ingredients which are particularly preferred are as follows: 1-menthol, racemic menthol, menthone glycerol acetal (trade name: Frescolat® MGA), menthyl lactate (preferably 1-menthyl lactate, in particular 1-menthyl-1-lactate, trade name: Frescolat® ML), 3-menthoxypropane-1,2-diol, 2-hydroxyethyl menthyl carbonate, 2-hydroxypropyl menthyl carbonate.

Malodor counteracting agents include an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, zinc undecenylate, β-naphthyl methyl ether, β-naphthyl ketone, benzyl acetone. They may include mixture of hexahydro-4,7-methanoinden-5-yl propionate and hexahydro-4,7-methanoinden-6-yl propionate; 4-(2,6,6-trimethyl-2-cyclohexen-1-yl)-3-methyl-3-buten-2-one; 3,7-dimethyl-2,6-nonadien-1-nitrile; dodecahydro-3a,6,6,9a-tetramethylnaphtho(2,1-b)furan; ethylene glycol cyclic ester of n-dodecanedioic acid; 1-cyclohexadecen-6-one; 1-cycloheptadecen-10-one; and corn mint oil. They may also include 1-cyclohexylethan-1-yl butyrate; 1-cyclohexylethan-1-yl acetate; 1-cyclohexylethan-1-ol; 1-(4'-methylethyl)cyclohexylethan-1-yl propionate; and 2'-hydroxy-1'-ethyl(2-phenoxy)acetate each of which compound is marketed under the trademark VEILEX by International Flavors & Fragrances Inc. More suitable malodor counteracting agents are polymers containing an α-keto, benzaldehyde, or α,β-unsaturated carbonyl moiety, such as those described in US Application Publications 2012/0294821, 2013/0101544 and 2013/0101545.

Vitamins include any vitamin, a derivative thereof and a salt thereof. Examples are as follows: vitamin A and its analogs and derivatives (e.g., retinol, retinal, retinyl palmitate, retinoic acid, tretinoin, and iso-tretinoin, known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like).

The products according to the invention can contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

Anti-inflammatory agents include, e.g., methyl salicylate, aspirin, ibuprofen, and naproxen. Additional anti-inflammatories useful in topical applications include corticosteroids, such as, but not limited to, flurandrenolide, clobetasol propionate, halobetasol propionate, fluticasone propionate, betamethasone dipropionate, betamethasone benzoate, betamethasone valerate, desoximethasone, dexamethasone, diflorasone diacetate, mometasone furoate, amcinodine, halcinonide, fluocinonide, fluocinolone acetonide, desonide, triamcinolone acetonide, hydrocortisone, hydrocortisone acetate, fluoromethalone, methylprednisolone, and predinicarbate.

Anesthetics that can be delivered locally include benzocaine, butamben, butamben picrate, cocaine, procaine, tetracaine, lidocaine and pramoxine hydrochloride.

Suitable analgesics include, but are not limited to, ibuprofen, diclofenac, capsaicin, and lidocaine.

Non-limiting examples of anti-fungal agents include micanazole, clotrimazole, butoconazole, fenticonasole, tioconazole, terconazole, sulconazole, fluconazole, haloprogin, ketonazole, ketoconazole, oxinazole, econazole, itraconazole, torbinafine, nystatin and griseofulvin.

Non-limiting examples of antibiotics include erythromycin, clindamycin, synthomycin, tetracycline, metronidazole and the like.

Exemplary antibacterials include bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2,4,4'-trichloro-2' hydroxy-diphenylether), thymol, and triclocarban.

Examples of antioxidants include beta-carotene, vitamin C (Ascorbic Acid) or an ester thereof, vitamin A or an ester thereof, vitamin E or an ester thereof, lutein or an ester thereof, lignan, lycopene, selenium, flavonoids, vitamin-like antioxidants such as coenzyme Q10 (CoQ10) and glutathione, and antioxidant enzymes such as superoxide dismutase (SOD), catalase, and glutathione peroxidase.

Anti-viral agents include, but are not limited to, famcyclovir, valacyclovir and acyclovir.

Non-limiting examples of anti-parasitic agents include scabicedes, such as permethrin, crotamiton, lindane and ivermectin.

Anti-infectious and anti-acne agents include, but are not limited to, benzoyl peroxide, sulfur, resorcinol and salicylic acid.

Dermatological active ingredients useful in topical applications include, e.g., jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate.

Examples of enzymes and co-enzymes useful for topical application include co-enzyme Q10, papain enzyme, lipases, proteases, superoxide dismutase, fibrinolysin, desoxyribonuclease, trypsin, collagenase and sutilains.

Non-limiting examples of skin whitening agents include hydroquinone and monobenzone.

Anti-histamines include, but are not limited to, chlorpheniramine, brompheniramine, dexchlorpheniramine, tripolidine, clemastine, diphenhydramine, prometazine, piperazines, piperidines, astemizole, loratadine and terfonadine.

Non-limiting examples of chemotherapeutic agents include 5-fluorouracil, masoprocol, mechlorethamine, cyclophosphamide, vincristine, chlorambucil, streptozocin, methotrexate, bleomycin, dactinomycin, daunorubicin, coxorubicin and tamoxifen.

Non-limiting examples of insect repellents include pediculicides for treatment of lice, such as pyrethrins, permethrin, malathion, lindane and the like.

Sunscreen Actives for example: for example, oxybenzone, octylmethoxy cinnamate, butylmethoxy dibenzoyln ethane, p-aminobenzoic acid and octyl dimethyl-p-aminobenzoic acid.

In some embodiments, the amount of encapsulated active material is from 0.5% to 80% (e.g., 5 to 65%, 15 to 55%, 20 to 45%, and 25 to 40%) by weight of the capsule slurry as prepared; and the amount of the capsule wall is from 0.5% to 25% (e.g., 1.5 to 15% and 2.5 to 10%) also by weight of the capsule slurry as prepared. In other embodiments, the amount of the encapsulated active material is from 15% to 99.5% (e.g., 50 to 98% and 30 to 95%) by weight of the capsule, and the amount of the capsule wall is from 0.5% to 85% (e.g., 2 to 50% and 5 to 70%) by weight of the capsule.

Core Modifiers.

In addition to the fragrance materials, the present invention also contemplates the incorporation of other core modifiers including solvents, emollients, and particles or polymeric core modifiers into the oil core.

Suitable solvents can be hydrophobic materials that are miscible in the active materials. The solvent materials serve to increase the compatibility of various active materials, increase the overall hydrophobicity of the mixture containing the active materials, influence the vapor pressure, or serve to structure the mixture. Useful solvents include those having reasonable affinity for the active materials and a C log P greater than 2.5, preferably greater than 3.5 and more preferably greater than 5.5. In some embodiments, the solvent is combined with the active materials that have C log P values as set forth above. It should be noted that selecting a solvent and active material with high affinity for each other will result in improvement in stability. Suitable solvents include triglyceride oil, mono and diglycerides, mineral oil, silicone oil, diethyl phthalate, polyalpha olefins, castor oil, isopropyl myristate, mono-, di- and tri-esters and mixtures thereof, fatty acids, and glycerine. The fatty acid chain can range from $C_4$-$C_{26}$ and can have any level of unsaturation. For instance, one of the following solvents can be used: capric/caprylic triglyceride known as NEOBEE M5 (Stepan Corporation); the CAPMUL series by Abitec Corporation (e.g., CAPMUL MCM); isopropyl myristate; fatty acid esters of polyglycerol oligomers, e.g., R2CO—[OCH$_2$—CH(OCOR1)-CH$_2$O—]$_n$, where R1 and R2 can be H or $C_4$-$C_{26}$ aliphatic chains, or mixtures thereof, and n ranges between 2 and 50, preferably 2 and 30; nonionic fatty alcohol alkoxylates like the NEODOL surfactants by BASF; the dobanol surfactants by Shell Corporation or the BIO-SOFT surfactants by Stepan, wherein the alkoxy group is ethoxy, propoxy, butoxy, or mixtures thereof and said surfactants can be end-capped with methyl groups in order to increase their hydrophobicity; di- and tri-fatty acid chain containing nonionic, anionic and cationic surfactants, and mixtures thereof; fatty acid esters of polyethylene glycol, polypropylene glycol, and polybutylene glycol, or mixtures thereof; polyalphaolefins such as the EXXONMOBIL PURESYM PAO line; esters such as the EXXONMOBIL PURESYN esters; mineral oil; silicone oils such polydimethyl siloxane and polydimethyl-cyclosiloxane; diethyl phthalate; di-octyl adipate and di-isodecyl adipate. In certain embodiments, ester oils have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

While no solvent is needed in the oil core, it is preferable that the level of solvent in the core of the capsule product is 80 wt % or less, preferably 50 wt % or less (e.g., 0-20 wt % and 0.5-15 wt %).

When the active material is a fragrance, it is preferred that fragrance ingredients within a fragrance having a C log P of 0.5 to 15 are employed. For instance, the ingredients having a C log P value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater and 90% or greater) by the weight of the fragrance.

In some embodiments, it is preferred that a fragrance having a weight-averaged C log P of 2.5 and greater (e.g., 3 or greater, 2.5 to 7, and 2.5 to 5) is employed. The weight-averaged C log P is calculated as follows:

$$C \log P = \{Sum[(Wi)(C \log P)i]\}/\{Sum\ Wi\},$$

in which Wi is the weight fraction of each fragrance ingredient and (C log P)i is the C log P of that fragrance ingredient.

As an illustration, it is preferred that greater than 60 weight percent, preferably greater than 80 and more preferably greater than 90 weight percent of the fragrance chemicals have C log P values of greater than 2, preferably greater than 3.3, more preferably greater than 4, and even more preferably greater than 4.5.

Those skilled in the art will appreciate that many fragrances can be created employing various solvents and fragrance ingredients. The use of relatively low to intermediate C log P fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high log P materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

Other emollients and core modifiers include:

i) Triglycerides and modified triglycerides. These include vegetable oils such as jojoba, soybean, canola, sunflower, safflower, rice bran, avocado, almond, olive, sesame, persic, castor, coconut, and mink oils.

ii) Ester oils have at least one ester group in the molecule. One type of common ester oil useful in the present invention are the fatty acid mono and polyesters such as cetyl octanoate, octyl isonanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

iii) Ester oil is liquid polyester formed from the reaction of a dicarboxylic acid and a diol. Examples of polyesters suitable for the present invention are the polyesters marketed by ExxonMobil under the trade name PURESYN ESTER®, hydrophobic plant extracts;

iv) Silicones: for example linear and cyclic polydimethylsiloxanes, amino-modified, alkyl, aryl, and alkylaryl silicone oils v) Low/non volatile hydrocarbons vi) Nanoscale solid particulate materials such as those disclosed in U.S. Pat. No. 7,833,960 may be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), magenase (Mn), iron (Fe), nickel (Ni), cobalt (Co), copper (Cu), gold (Au), silver (Ag), platinum (Pt) and palladium(Pd). Other suitable metallic particles can be selected the periodic table as long as their physical dimension falls into the prescribed region.

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

vii) Polymeric Core Modifiers. It has also been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the active material and other solvent. Preferably, the polymer also thickens or gels the core, thus further reducing diffusion. Polymers may be selected from the non-limiting group below: Copolymers of ethylene. Copolymers of ethylene and vinyl acetate (Elvax polymers by DOW Corporation). Copolymers of ethylene and vinyl alcohol (EVAL polymers by Kuraray). Ethylene/ Acrylic elastomers such as Valnac polymers by Dupont). Poly vinyl polymers, such as poly vinyl acetate. Alkyl- substituted cellulose, such as ethyl cellulose (Ethocel made by DOW Corporation), hydroxypropyl celluloses (Klucel polymers by Hercules); cellulose acetate butyrate available from Eastman Chemical. Polyacrylates. Examples being (i) Amphomer, Demacryl LT and Dermacryl 79, made by National Starch and Chemical Company, (ii) the Amerhold polymers by Amerchol Corporation, and (iii) Acudyne 258 by ISP Corporation. Copolymers of acrylic or methacrylic acid and fatty esters of acrylic or methacrylic acid. These are side-chain crystallizing. Typical polymers of this type are those listed in U.S. Pat. Nos. 4,830,855, 5,665,822, 5,783, 302, 6,255,367 and 6,492,462. Examples of such polymers are the Intelimer Polymers, made by Landec Corporation. Polypropylene oxide. Polybutylene oxide of poly(tetrahy- drofuran). Polyethylene terephthalate. Polyurethanes (Dy- nam X by National Starch) Alkyl esters of poly(methyl vinyl ether)-maleic anhydride copolymers, such as the Gantrez copolymers and Omnirez 2000 by ISP Corporation. Carbox- ylic acid esters of polyamines. Examples of this are ester- terminated polyamide (ETPA) made by Arizona Chemical Company. Poly vinyl pyrrolidone (Luviskol series of BASF). Block copolymers of ethylene oxide, propylene oxide and/or butylenes oxide. These are known as the Pluronic and Synperonic polymers/dispersants by BASF. Another class of polymers include polyethylene oxide-co- propyleneoxide-co-butylene oxide polymers of any ethylene oxide/propylene oxide/butylene oxide ratio with cationic groups resulting in a net theoretical positive charge or equal to zero (amphoteric). The general structure is:

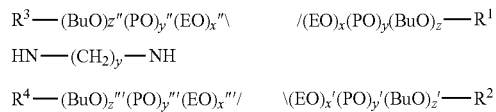

where $R^1$, $R^2$, $R^3$, and $R^4$ are independently H or any alkyl or fatty alkyl chain group. Examples of such polymers are the commercially known as TETRONICS by BASF Corpo- ration.

viii) Sacrificial core ingredients can also be included. These ingredients are designed to be lost during or after manufacture and include, but are not limited to, highly water soluble or volatile materials.

ix) Nonlimiting examples of a solubility modifier include surfactants (e.g., SLS and Tween 80), acidic compounds (e.g., mineral acids such as sulfuric acid, hydrochloric acid, nitric acid, and phosphoric acid, and carboxylic acids such as acetic acid, citric acid, gluconic acid, glucoheptonic acid, and lactic acid), basic compounds (e.g., ammonia, alkali metal and alkaline earth metal hydroxides, primary, second- ary, or tertiary amines, and primary, secondary, or tertiary alkanolamines), ethyl alcohol, glycerol, glucose, galactose, inositol, mannitol, glactitol, adonitol, arabitol, and amino acids.

x) Density modifiers can be used to adjust the density of the capsule slurry and/or the oil core so that the capsule composition has a substantially uniform distribution of the capsules using known density modifiers or technologies such as those described in Patent Application Publications WO 2000/059616, EP 1 502 646, and EP 2 204 155. Suitable density modifiers include hydrophobic materials and mate- rials having a desired molecular weight (e.g., higher than 12,000), such as silicone oils, petrolatums, vegetable oils, especially sunflower oil and rapeseed oil, and hydrophobic solvents having a desired density (e.g., less than 1,000 $Kg/m^3$ at 25° C., such as limonene and octane.

xi) In some embodiments, a stabilizer (e.g., a colloidal stabilizer) is added to a capsule composition to stabilize the emulsion and/or capsule slurry. Examples of colloidal sta- bilizers are polyvinyl alcohol, cellulose derivatives such hydroxyethyl cellulose, polyethylene oxide, copolymers of polyethylene oxide and polyethylene or polypropylene oxide, or copolymers of acrylamide and acrylic acid. More stabilizing agents are described below.

xii) Viscosity control agents (e.g., suspending agents), which may be polymeric or colloidal (e.g., modified cellu- lose polymers such as methylcellulose, hydroxyethylcellu- lose, hydrophobically modified hydroxyethylcellulose, and cross-linked acrylate polymers such as Carbomer, hydro- phobically modified polyethers) can be included in the capsule composition, in the capsule core or wall, or in the capsule slurry outside the capsules. Exemplary Carbomers include the acrylates/C10-C30 alkyl acrylate crosspolymers commercially available from Lubrizol under the Carbopol® ETD product line. These polymers can be included in the compositions of this invention at a level of 0.05-3% (e.g., 0.2-0.3%). Optionally, silicas, either hydrophobic or hydro- philic, can be included at a concentration from 0.01 to 20%, more preferable from 0.5 to 5%, by the weight of the capsule composition. Examples of hydrophobic silicas include silanols, surfaces of which are treated with halogen silanes, alkoxysilanes, silazanes, and siloxanes, such as SIPERNAT D17, AEROSIL R972 and R974 available from Degussa. Exemplary hydrophilic silicas are AEROSIL 200, SIPER- NAT 22S, SIPERNAT 50S (available from Degussa), and SYLOID 244 (available from Grace Davison).

xiii) One or more humectants are optionally included to hold water in the capsule composition for a long period of time. Examples include glycerin, propylene glycol, alkyl phosphate esters, quaternary amines, inorganic salts (e.g., potassium polymetaphosphate, sodium chloride, etc.), poly- ethylene glycols, and the like.

Further suitable humectants, as well as viscosity control/ suspending agents, are disclosed in U.S. Pat. Nos. 4,428, 869, 4,464,271, 4,446,032, and 6,930,078. Details of hydro- phobic silicas as a functional delivery vehicle of active materials other than a free flow/anticaking agent are dis- closed in U.S. Pat. Nos. 5,500,223 and 6,608,017.

xiv) In some embodiments, one or more pH modifiers are included in the capsule composition to adjust the pH value of the capsule slurry and/or the capsule cores. The pH modifiers can also assist in the formation of capsule walls by changing the reaction rate of the crosslinking reactions that form the capsule walls. Exemplary pH modifiers include metal hydroxides (e.g., LiOH, NaOH, KOH, and $Mg(OH)_2$), metal carbonates and bicarbonates ($CsCO_3$ $Li_2CO_3$, $K_2CO_3$, $NaHCO_3$, and $CaCO_3$), metal phosphates/hydrogen phos- phates/dihydrogen phosphates, metal sulfates, ammonia, mineral acids (HCl, $H_2SO_4$, $H_3PO_4$, and $HNO_3$), carboxylic acids (e.g., acetic acid, citric acid, lactic acid, benzoic acid, and sulfonic acids), and amino acids.

One or more adjunct materials may be added to the capsule compositions.

The capsule compositions of this invention can also include one or more non-confined unencapsulated active materials from 0.01 to 50%, more preferably from 5 to 40%.

The level of solvent materials, particles, adjuncts, or core modifiers can be 0.01% to 25% (e.g., from 0.5% to 10%) or greater than 10% (e.g., greater than 30% and greater than 70%).

Deposition Aids.

Deposition aids can also be used to assist the deposition of capsules to surfaces such as fabric, hair or skin. Examples include but are not limited to anionically, cationically, non-ionically, or zwitterionically charged water-soluble polymers which can be added to polyurea or polyurethane capsules. These water-soluble polymers can also be amphoteric polymers with a ratio of cationic and anionic functionalities resulting in a net total charge of zero or positive, i.e., cationic. Those skilled in the art would appreciate that the charge of these polymers can be adjusted by changing the pH, depending on the product in which this technology is to be used. Any suitable method for coating the deposition aids onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (co-valently) grafted to the capsule or particle surface. Chemical modification of the capsule or particle surface is another way to optimize anchoring of the polymer coating to capsule or particle surface. Furthermore, the capsule and the polymer need to go to the desired interface and, therefore, need to be compatible with the chemistry (polarity, for instance) of that interface. Therefore, depending on which capsule chemistry and interface (e.g., cotton, polyester, hair, skin, wool), the polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from 1,000 to 1000,000,000, preferably from 5,000 to 10,000,000. As used herein, molecular weight is provided as weight average molecular weight.

Particular examples of cationic polymers that can be used to coat the polyurea or polyurethane capsule include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDAD-MAC on cellulose, e.g., CELQUAT L-200 (POLYQUATERNIUM-4), POLYQUATERNIUM-10 and POLYQUATERNIUM-24, commercially available from National Starch, Bridgewater, N.J. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

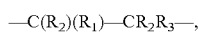

—C($R_2$)($R_1$)—C$R_2R_3$—, wherein, $R_1$ is a $C_1$-$C_{25}$ alkane or H, wherein the number of double bonds ranges from 0-5, $R_1$ is an alkoxylated fatty alcohol with any alkoxy carbon-length of $C_1$-$C_{25}$, or $R_1$ is a liquid crystalline moiety that can provide the polymer with thermotropic liquid crystalline properties;

$R_2$ is H or $CH_3$; and $R_3$ is —Cl, —$NH_2$ (i.e., polyvinyl amine or its copolymers with N-vinyl formamide.

Such polyvinyl polymers are sold under the name LUPAMIN 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

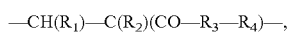

—CH($R_1$)—C($R_2$)(CO—$R_3$—$R_4$)—, wherein, $R_1$ is a $C_1$-$C_{25}$ alkane from or H with a number of double bonds from 0-5, $R_1$ is an alkoxylated fatty alcohol with a $C_1$-$C_{25}$ alkyl chain length, or $R_1$ is a liquid crystalline moiety that provides the polymer with thermotropic liquid crystalline properties;

$R_2$ is H or $CH_3$;

$R_3$ is a $C_1$-$C_{25}$ alkyl alcohol or an alkylene oxide with any number of double bonds, or $R_3$ may be absent such that the C=O bond is (via the C-atom) directly connected to $R_4$; and $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —OH, —COOH alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAFQUAT HS100.

Another group of polymers that can be used are those that contain cationic groups in the main chain or backbone. Included in this group are:

i) polyalkylene imines such as polyethylene imine, commercially available as LUPASOL from BASF. Any molecular weight and any degree of crosslinking of this polymer can be used in the present invention;

ii) ionenes as disclosed in U.S. Pat. Nos. 4,395,541 and 4,597,962;

iii) adipic acid/dimethyl amino hydroxypropyl diethylene triamine copolymers, such as CARTARETIN F-4 and F-23, commercially available from Sandoz;

iv) polymers of the general formula: $—[N(CH_3)_2—(CH_2)_x—NH—(CO)—NH—(CH_2)_y—N(CH_3)_2)—(CH_2)_z—O—(—CH_2)_p]_n—$, with x, y, z, p=1-12, and n according to the molecular weight requirements. Examples are Polyquaternium 2 (MIRAPOL A-15), Polyquaternium-17 (MIRAPOL AD-1), and Polyquaternium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: $—Si(R_1)(R_2)—O—]_x—[Si(R_3)(R_2)—O—]_y—$ where $R_1$ is a $C_1$-$C_{25}$ alkane or H with the number of double bonds from 0-5, aromatic moieties, polysiloxane grafts, or mixtures thereof. $R_1$ can also be a liquid crystalline moiety that can provide the polymer with thermotropic liquid crystalline properties. $R_2$ can be H or $CH_3$; and $R_3$ can be $—R_1—R_4$, where $R_4$ can be $—NH_2$, $—NHR_1$, $—NR_1R_2$, $—NR_1R_2R_6$ (where $R_6=R_1$, $R_2$, or $—CH_2—COOH$ or its salt), $—NH—C(O)—$, $—COOH$, $—COO—$ alkali salt, any C1-25 alcohol, $—C(O)—NH_2$ (amide), $—C(O)—N(R_2)(R_2')(R_2")$, sulfobetaine, betaine, polyethylene oxide, poly(ethyleneoxide/propylene oxide/butylene oxide) grafts with any end group, H, $—OH$, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-$R_5$ or naphthalene-$R_6$ where $R_5$ and $R_6$ are $R_1$, $R_2$, $R_3$, sulfonic acid or its alkali salt or organic counter ion. $R_3$ can also be $—(CH_2)_x—O—CH_2—CH(OH)—CH_2—N(CH_3)_2—CH_2—COOH$ and its salts. Any mixture of these $R_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent EP0737183B1.

Furthermore, copolymers of silicones and polysaccharides and proteins can be used (e.g., those commercially available as CRODASONE brand products).

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazine-alkylene main chain copolymers disclosed by Kashiki and Suzuki (1986) *Ind. Eng. Chem. Fundam.* 25:120-125.

As indicated, the addition of hydrophobic polymers to the core can also improve stability by slowing diffusion of the fragrance from the core. The level of polymer is normally less than 80% of the core by weight, preferably less than 50%, and even more preferably less than 20%. The basic requirement for the polymer is that it be miscible or compatible with the other components of the core, namely the fragrance and other solvent. Preferably, the polymer also thickens or gels the core, thus further reducing diffusion.

Table 2 below shows polyquaternium polymers that can be used as deposition aids in this invention.

TABLE 2

Deposition Aids -- Cationic Polyquaternium Polymers

| Polyquaternium | Description | Commercial Products |
|---|---|---|
| 1 | Ethanol, 2,2',2"-nitrilotris-, polymer with 1,4-dichloro-2-butene and N,N,N',N'-tetramethyl-2-butene-1,4-diamine | Polyquad (Alcon) |
| 2 | Poly[bis(2-chloroethyl) ether-alt-1,3-bis[3-(dimethylamino)propyl]urea] | Mirapol A-15 |
| 4 | Hydroxyethyl cellulose dimethyl diallylammonium chloride copolymer; Diallyldimethylammonium chloride-hydroxyethyl cellulose copolymer | Celquat L-200, H-100, L-200 |
| 5 | Copolymer of acrylamide and quaternized dimethylammoniumethyl methacrylate | Merquat 5, RETEN (Hercules) |
| 6 | Poly(diallyldimethylammonium chloride) | Merquat 100, 106, Mirapol 100 |
| 7 | Copolymer of acrylamide and diallyldimethylammonium chloride | Merquat 550, 550L, 550PR, S, 7SPR, 740, 2200, Mirapol 550, Polyquart 770/NA, Conditioneze 7 |
| 8 | Methyl and Stearyl Dimethylaminoethyl Methacrylate Quaternized with Dimethyl Sulfate | |
| 9 | Polydimethylaminoethyl Methacrylate Quaternized with Methyl Bromide | |
| 10 | Quaternized hydroxyethyl cellulose | Merquat 10, Celquat SC-230M, SC-240C, SC-140C, Ucare Polymer |

TABLE 2-continued

Deposition Aids -- Cationic Polyquaternium Polymers

| Polyquaternium | Description | Commercial Products |
|---|---|---|
| 11 | Copolymer of vinylpyrrolidone and quaternized dimethylaminoethyl methacrylate | Luviquat PQ 11PN, Gafquat 775N, 440, 734, 775 |
| 12 | 2-Propenoic Acid, 2-Methyl-, Decahydro-1,4-Dimethyl-7-(1-Methylethyl)-1-Phenanthrenyl)Methyl Ester, Polymer with 2-(Diethylamino)Ethyl 2-Methyl-2-Propenoate and Ethyl 2-Methyl-2-Propenoate, compd. with Dimethyl Sulfate | |
| 13 | 2-Propenoic Acid, 2-Methyl-, 2-(Diethylamino)Ethyl Ester, Polymer with Ethyl 2-Methyl-2-Propenoate and 9-Octadecenyl 2-Methyl-2-Propenoate, compd. with Dimethyl Sulfate | |
| 14 | Ethanaminium, N,N,N-Trimethyl-2-[(2-Methyl-1-Oxo-2-Propenyl)Oxy]-, Methyl Sulfate, Homopolymer | |
| 15 | Ethanaminium, N,N,N-Trimethyl-2-[(2-Methyl-1-Oxo-2-Propenyl)Oxy]-, Chloride, Polymer with 2-Propenamide | Rohagit KF 720F (Rohm GmbH) |
| 16 | Copolymer of vinylpyrrolidone and quaternized vinylimidazole | Luviquat FC 370, HM 552, Style, FC 550, Excellence |
| 17 | Poly(Oxy-1,2-Ethanediyl (Dimethyliminio)-1,3-Propanediylimino(1,6-Dioxo-1,6-Hexanediyl)Imino-1,3-Propanediyl-(Dimethyliminio)-1,2-Ethanediyl Dichloride | Mirapol AD |
| 18 | Poly[oxy-1,2-ethanediyl(dimethyliminio)-1,3-propanediylimino-(1,6-dioxo-1,6-heptanediyl)imino-1,3-propanediyl-(dimethyliminio)-1,2-ethanediyl dichloride] | Luviquat 500 |
| 19 | Ethenol, polymer with aminomethyloxirane | Arlatone PQ-220 (ICI Americas) |
| 20 | Ethenyl octadecyl ether, polymer with aminomethyloxirane | Arlatone PQ-225 |
| 22 | Copolymer of Acrylic Acid and Diallyldimethylammonium Chloride | Merquat 280, 281, 280SD, 295 |
| 24 | Cellulose, 2-[2-Hydroxy-3-(Trimethylammonio)Propoxy]Ethyl Ether, Chloride (Similar to PQ-10) | Quatrisoft Polymer LM-200 (Dow Chemical) |
| 27 | Hexanediamide, N,N'-bis(3-(Dimethylamino)Propyl)-, Polymer with N,N'-bis(3-Dimethylamino)Propyl Urea and 1,1'-Oxybis(2-Chloroethane), Block | |
| 28 | Copolymer of vinylpyrrolidone and methacrylamidopropyl trimethylammonium | Gafquat HS-100, Conditioneze NT-10 |
| 29 | Chitosan, 2,3-Dihydroxypropyl-2-Hydroxy-3-(Trimethylammonio)Propyl Ether, Chloride | Quaternized Chitosan |
| 30 | Ethanaminium, NCarboxymethyl)-N,N-Dimethyl-2-((2-Methyl-1-Oxo-2-Propenyl)Oxy)-, Inner Salt, Polymer with Methyl 2-Methyl-2-Propenoate | Mexomere PX (Chimex) |
| 31 | 2-Propenenitrile, Homopolymer, Hydrolyzed, Block, Reaction Products with N,N-Dimethyl-1,3-Propanediamine, Di-Et Sulfate-Quaternized | Hypan QT100 (Lipo) |
| 32 | Poly(acrylamide 2-methacryloxyethyltrimethyl ammonium chloride) | Cosmedia CTC (Cognis GmbH) - PQ-32 + other, Salcare SC92 (Ciba Corp.) PQ-32 + other |
| 33 | Ethanaminium, N,N,N-Trimethyl-2-[1-Oxo-2-Propenyl)Oxy]-, Chloride, Polymer with 2-Propenamide | Lanoquat DES-50, Ultimer CG-200 (Nalco), Sepigel Quat33 (Seppic) - PQ-33 + other |
| 34 | Poly(diethyliminio-1,3-propanediyldimethyliminio-1,3-propanediyl dibromide) | Mexomere PAK (Chimex) |
| 35 | Ethanaminium, N-carboxymethyl-N,N-dimethyl-2-(2-methyl-1-oxo-2-propenyloxy)-, inner salt, polymer with N,N,N-trimethyl-2-(2-methyl-1-oxo-2-propenyloxy)ethanaminium methyl sulfate | Plex 3074 L (Rohm GmbH) |

TABLE 2-continued

Deposition Aids -- Cationic Polyquaternium Polymers

| Polyquaternium | Description | Commercial Products |
|---|---|---|
| 36 | 2-Propenoic Acid, 2-Methyl-, 2-(Dimethylamino)Ethyl Ester, Polymer with Methyl 2-Methyl-2-Propenoate, compd. with Dimethyl Sulfate | Plex 4739L (Rohm GmbH) |
| 37 | N,N,N-Trimethyl-2-[(Methyl-1-Oxo-2-Propenyl)Oxy]Ethanaminium Chloride, Homopolymer | Ultragel 300 (Cognis), Synthalen CN, CR, CU (3V Group), Syntran PC 5320 (Interpolymer) |
| 39 | 2-Propen-1-aminium, N,NDimethyl-N-2-Propenyl-, Chloride, Polymer with 2-Propenamide and 2-Propenoic Acid | Merquat 3940, PLUS-3330, PLUS-3331, 3331PR |
| 42 | Poly[oxyethylene(dimethyliminio)ethylene (dimethylimino)ethylene dichloride] | Busan 1507 (Buckman Labs) |
| 43 | polymeric quaternary ammonium salt formed from acrylamide, acrylamidopropyltrimonium chloride, 2-amidopropylacrylamide sulfonate, and DMAPA monomers | Genamin PQ 43 (Clariant Functional Chemicals), Bozequat 4000 (Clariant) |
| 44 | Poly(2-oxopyrrolidin-1-ylethylene, 3-methylimidazolium-1-ylethylene methyl sulfate) | Luviquat Ultracare, MS 370 (BASF), Softenol PQ44 (Zdchimmer & Schwarz Italianat S.p.A) |
| 45 | Glycine, N-methyl-N-[2-[(2-methyl-1-oxo-2-propenyl)oxy]ethyl]-, polymer with 2-(dimethylamino)ethyl 2-methyl-2-propenoate, compound with dimethyl sulfate | Plex 3073L (Rohm GmbH) |
| 46 | 1H-Imidazolium, 1-Ethenyl-3-Methyl-, Methyl Sulfate, Polymer with 1-Ethenyl-hexahydro-2H-Azepin-2-one and 1-Ethenyl-2-Pyrrolildinone | Luviquat Hold |
| 47 | 1-Propanaminium, N,N,NTrimethyl-3-((2-Methyl-1-Oxo-2-Propenyl)Amino)-, Chloride, Polymer with Methyl 2-Propenoate and 2-Propenoic Acid | Merquat 2001, 2001N |
| 48 | Polymeric quaternary ammonium salt of formed from methacryloyl ethyl betaine, 2-hydroxyethyl methacrylate and methacryloyl ethyl trimethyl ammonium chloride | Plascize L-450 (Goo Chemical) |
| 49 | polymeric quaternary ammonium salt formed by the reaction of methacryloyl ethyl betaine, PEG-9 methacrylate and methacryloyl ethyl trimethyl ammonium chloride | Plascize L-440 (Goo Chemical) |
| 50 | Carboxylatoethyldimethylammonioethyl 2-methyl-2-propenoate homopolymer | Plascize L-401 (Goo Chemical) |
| 51 | 3,5,8-Triox-4-Phosphaundec-10-en-1-aminium, 4-Hydroxy-N,N,N,10-Tetramethyl-9-Oxo, Inner Salt, 4-Oxide, Polymer with Butyl 2-Methyl-2-Propenoate | Lipidure PMB (NOF) |
| 53 | Acrylic Acid/Acrylamide/Methacryl-amidopropyltrimonium Chloride Copolymer | Merquat 2003PR |
| 54 | Aspartic acid, polymer with C6-18 alkylamine, 3-dimethylaminopropylamine and sodium chloroacetate | Quilty-Hy (Mitsui) |
| 55 | 1-Dodecanaminium, N,NDimethyl-N-[3-[(2-Methyl-1-Oxo-2-Propenyl)-Amino-Propyl]-, Chloride, Polymer with N-[3-(Dimethylamino)Propyl]-2-Methyl-2-Propenamide and 1-Ethenyl-2-Pyrrolidinone | Styreze W |
| 56 | 5-Isocyanato-1-(isocyanatomethyl)-1,3,3-trimethylcyclohexane, polymer with 1,3-butanediol and bis(2-hydroxyethyl)di-methylammonium methyl sulfate | Hairrol UC-4 (Sanyo Chemical) |
| 57 | 12-Hydroxy-9(Z)-octadecenamidopropyl-trimethylammonium chloride, polymers with *ricinus communis* (castor) oil, isooctdecanoic acid and butandioic acid | Zenigloss Q (Zenitech) |

TABLE 2-continued

Deposition Aids -- Cationic Polyquaternium Polymers

| Polyquaternium | Description | Commercial Products |
|---|---|---|
| 58 | 2-Propenoic Acid, Methyl Ester, Polymer with 2,2-Bis[(2-Propenyloxy)Methyl]-1-Butanol and Diethenylbenzene, Reaction Products with N,NDimethyl-1,3-Propanediamine, Chloromethane-Quaternized | Lowenol Conditioner PWW (Lowenstein) -PQ-58 and Wheat Protein |
| 59 | Poly(20,25-dioxo-2,5,10,15,18-pentamethyl-10-(2-hydroxy-3-(3-(3-phenyl-2-propenamido)propyldimethylammonio)propyl)-10-azonia-1,4,7,13,16,19-hexaoxa-pentacosanediyl) chloride | Crodasorb UV-HPP (Croda, Inc.) - PQ-59 and Butylene Glycol |
| 60 | 9-Octadecenoic Acid, 12-Hydroxy-, [(2-Hydroxyethyl)-Imino]Di-2,1-Ethanediyl Ester, Polymer with 5-Isocyanato-1-(Isocyanatomethyl)-1,3,3-Trimethyl-cyclohexane, Compd. with Diethyl Sulfate | Polylipid PPI-RC (Alzo/Bernel) - PQ-60 and Propylene Glycol |
| 61 | 2-Methyl-2-propenoyloxyethyl N,N,N-trimethylammonioethyl phosphate inner salt, polymer with octadecyl 2-methyl-2-propenoate | Lipidure-S (NOF) |
| 62 | Polymeric quaternary ammonium salt of butyl methacrylate, polyethylene glycol methyl ether methacrylate, ethylene glycol dimethacrylate and 2-methacryloylethyl trimonium chloride with 2,2'-azobis(2-methyl propionamidine)dihydrochloride | Nanoaquasome (Amore Pacific/Kyung-do) |
| 63 | polymeric quaternary ammonium salt formed by acrylamide, acrylic acid and ethyltrimonium chloride acrylate | Finquat (Innospec), Octacare PQ63 (Innospec Edison, NJ), OF-308 (WSP Chemical & Technology) |
| 64 | 2-Methyl-2-propenoyloxyethyl N,N,N-trimethylammonioethyl phosphate inner salt, polymer with 2-hydroxy-3-(2-methyl-2-propenoyl)oxypropyltrimethyl-ammonium chloride | Lipidure-C (NOF) |
| 65 | 2-Methyl-2-propenoyloxyethyl N,N,N-trimethylammonioethyl phosphate inner salt, polymer with butyl 2-methyl-2-propenoate and sodium 2-methyl-2-propenoate | Lipidure-A (NOF) |
| 66 | 5-Isocyanato-1-(isocyanatomethyl)-1,3,3-trimethylcyclohexane, polymer with di(hydroxypolymethylene) benzene-dicarboxylate and ethylbis(2-hydroxy-ethyl)methylammonium ethyl sulfate | WBR-2925C (Taisei) - PQ-66 and Methyl Pyrrolidone |
| 67 | 2-Hydroxyethyl cellulose ether, reaction products with N,N,N-trimethyl-N-oxiranylmethylammonium chloride and N-dodecyl-N,N-dimethyl-N-oxiranylmethylammonium chloride | Softcat (Dow Chemical) |
| 68 | 1-Ethenyl-2-pyrrolidinone, polymer with 1-ethenylimidazole and 1-ethenyl-3-methylimidazolium methyl sulfate | Luviquat Supreme |
| 69 | polymeric quaternary ammonium salt composed of vinyl caprolactam, vinylpyrrolidone, dimethylaminopropyl methacrylamide (DMAPA), and methacryloylaminopropyl lauryldimonium chloride | Aquastyle 100, 300 (ISP) |
| 70 | polymeric quaternary ammonium salt consisting of an ethoxylated, propoxylated stearyl amine condensed with adipic acid and dilinoleic acid and quaternized with dimethyl sulfate | Lustreplex (Croda) |
| 71 | | ColaMoist 300P (Colonial Chemical Inc) |
| 72 | polymeric quaternary ammonium salt of hydroxethylcellulose reacted with a coco-alkyl dimethyl ammonium substituted epoxide | Mirustyle CP (Croda) |
| 73 | polymeric quaternary ammonium salt consisting of propyltrimonium chloride acrylamide, ethyltrimonium chloride methacrylate and dimethylacrylamide monomers; Propanaminium, N,N,N-trimethyl-3-(2-propenamido)-, chloride, polymer with N,N,N-trimethyl-2-(2- | Diaformer C-802, C-823 (Mitsubishi Chem), Diasleek C-802, C-823 (Mitsubishi Chem) |

TABLE 2-continued

Deposition Aids -- Cationic Polyquaternium Polymers

| Polyquaternium | Description | Commercial Products |
|---|---|---|
| | methyl-2-propenoyloxy)ethanaminium chloride and N,N-dimethyl-2-propenamide | |
| 74 | | Mirapol PB 20 (Rhodia) |
| | | Polycare Boost (Rhodia) |
| 75 | O-(2-Hydroxy-2-trimethylammonio-propyl)starch chloride, reaction products with O-(3-dodecyldimethylammonio-2-hydroxypropyl)starch chloride | Amylomer Cat 220EMU (Grafe Chemie) |
| 76 | | Mirapol AT-1 (Rhodia) |
| 77 | Cocoglucoside Crosspolymer Hydroxypropyltrimonium Chloride | Colonial Poly SugaQuat TM-8610P (Colonial Chemical Inc) |
| 78 | Decylglucoside Crosspolymer Hydroxypropyl Laurdimonium Chloride | Colonial Poly SugaQuat L-1010P (Colonial Chemical Inc) |
| 79 | Decylglucoside Crosspolymer Hydroxypropyl Steardimonium Chloride | Colonial Poly SugaQuat S-1010P (Colonial Chemical Inc) |
| 80 | Laurylglucoside Crosspolymer Hydroxypropyl Laurdimonium Chloride | Colonial Poly SugaQuat L-1210P (Colonial Chemical Inc) |
| 81 | Laurylglucoside Crosspolymer Hydroxypropyl Steardimonium Chloride | Colonial Poly SugaQuat S-1210P (Colonial Chemical Inc) |
| 82 | Laurylglucoside Crosspolymer Hydroxypropyltrimonium Chloride | Colonial Poly SugaQuat TM-1218P (Colonial Chemical Inc) |
| 84 | polymeric quaternary ammonium salt of acrylamidopropyltrimethylammonium chloride, trimethylaminoethyl methacrylate, dimethylacrylamide and hydroxyethylmethacrylate | Diasleek C-824 (Mitsubishi Chemical) |
| 85 | polymeric quaternary ammonium salt of acrylamidopropyltrimethylammonium chloride, dimethylacrylamide and hydroxyethylmethacrylate | Diasleek C-825 (Mitsubishi Chemical) |
| 86 | polymeric quaternary ammonium salt of vinylpyrrolidone, 1-methyl-3-vinylimidazoline chloride, vinylimidazole and methacrylic acid | Luvigel Advanced (BASF) |
| 87 | polymeric quaternary ammonium salt of vinylpyrrolidone, vinylimidazole and diallyldimethyl ammonium chloride | Luviquat Sensation (BASF) |
| 88 | Poly(Dilinoleyldimonium hydroxypropyl)chlorides) | ColaQuat PDQ (Colonial Chemical Inc) |
| 89 | polymeric quaternary ammonium salt prepared by the reaction of t-butyl acrylate, vinyl pyrolidone, dimethylaminopropyl methacrylamide, methacrylic acid and ethyldimethyl[2-[(2-methyl-1-oxoallyl)oxy]ammonium ethyl sulfate, neutralized with orthophosphoric acid | (BASF) |
| 90 | polymeric quaternary ammonium salt of acrylamide and hydroxyethylcellulose quaternized with diallyldimethyl ammonium chloride | Hymoquat AK325R (Hymo Corporation) |
| 91 | polymeric quaternary ammonium salt of hydroxypropyl methacrylate and polyethylene glycol methacrylate quaternized with ethyltrimonium chloride methacrylate | Syntran 5500 (Interpolymer) - PQ-91 and PA |
| 92 | GLYCERYLAMIDOETHYL METHACRYLATE/STEARYL METHACRYLATE COPOLYMER | Ceracute-G (NOF) |
| 94 | polymeric quaternary ammonium salt consisting of acrylamide, dimethyl diallyl ammonium chloride and methacrylamidopropyltrimonium chloride monomers | (Toho) |
| 95 | copolymer of Zea Mays (Corn) Starch, Acrylic Acid and acrylamidopropyltrimethylammonium chloride monomers | Polyquart Ecoclean (Cognis) |
| 98 | | (Cognis GmbH) |
| 101 | | Deposilk Q1 (Air Products) |

Other suitable deposition aids include those described in US 2013/0330292, US 2013/0337023, US 2014/0017278.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine include L-ornithine and its salts/hydrates (e.g., monohydrochloride) and D-omithine and its salts/hydrates (e.g., monohydrochloride).

In certain embodiments of the invention, the capsule slurry is cured at a temperature greater than 55° C.; greater than 65° C.; greater than 75° C.; greater than 85° C.; greater than 95° C.; greater than 105° C. or greater than 120° C.

Capsules prepared in accordance with this invention preferably have a size in the range of from 0.01 to 1000 microns (e.g., 0.5 to 1000 microns, 1 to 200 microns, 0.5 to 150 microns, 2 to 50 microns, 5 to 25 microns, and 2 to 15 microns). The capsule distribution can be narrow, broad, or multi-modal.

In some embodiments, capsules are purified before use. Purification can be achieved by washing with water or an aqueous solution, diafiltration, and centrifugation. Suitable diafiltration processes are those described in US Patent Application Publication 2014/0134242 and Sheth et al., *J. of Membr. Sci.* 2003, 211.2, 251-61. The capsule slurry can also be washed with water until a neutral pH in the capsule slurry is achieved. For the purposes of the present invention, the capsule compositions can be washed using any conventional method including the use of a separatory funnel, filter paper, centrifugation and the like. The capsule suspension can be washed one, two, three, four, five, six, seven, eight, nine, ten or more times until a neutral pH, i.e., pH 7±0.5, is achieved. The pH of the purified capsules can be determined using any conventional method including, but not limited to pH paper, pH indicators, or a pH meter.

A capsule suspension of this invention is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium carbonate, sodium bicarbonate, sodium chloride, potassium carbonate, potassium bicarbonate, potassium chloride, and bi-sulphite salts.

The microcapsule composition of this invention can also be spray dried to a solid form. In a spray drying process, a spray dry carrier is added to a microcapsule composition to assist the removal of water from the slurry.

According to one embodiment, the spray dry carriers can be selected from the group consisting of carbohydrates such starch, as chemically modified starches and/or hydrolyzed starches, gums such as gum arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%.

Optionally, a free flow agent (anticaking agent) of silicas which may be hydrophobic (i.e. silanol surface treated with halogen silanes, alkoxysilanes, silazanes, siloxanes, etc. such as Sipernat D17, Aerosil R972 and R974 (available from Degussa), etc.) and/or hydrophilic such as Aerosil 200, Sipernat 22S, Sipernat 50S, (available from Degussa), Syloid 244 (available from Grace Davison), may be present from 0.01 to 10%, more preferable from 0.5 to 5%.

Humectants and viscosity control/suspending agents can also be added to facilitate spray drying. These agents are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

The spray drying inlet temperature is in the range of 150 to 240° C., preferably between 170 and 230° C., more preferably between 190 and 220° C.

In some embodiments, the spry dried microcapsule composition of this invention is a hybrid encapsulate formulation obtained by a method including the steps of preparing an aqueous starch solution; preparing an oil phase containing an active material (e.g., a fragrance oil); emulsifying the oil phase with an aqueous starch solution to obtain an emulsion; mixing the emulsion with a polyurea or polyurethane microcapsule suspension; and spray drying the mixture to obtain a hybrid encapsulate formulation.

In accordance with the present invention, a starch aqueous solution is intended to mean a starch solution in which the solvent is water. As is known in the art, starch is a carbohydrate composed of a large number of glucose units joined by glycosidic bonds. The starch of this invention can be obtained from seeds, roots or tubers, by wet grinding, washing, sieving and drying. Starches are predominantly obtained from corn, wheat and potato, and to a lesser extent, sources such as rice, sweet potato, sago and mung bean. The starch can be unmodified or chemically modified to allow the starch to function under conditions frequently encountered during processing or storage, such as high heat, high shear, low pH, oxidation, freeze/thaw and cooling. Such modifications include, but are not limited to acid treatment, alkaline treatment, bleaching, oxidation, enzyme treatment, acetylation, phosphorylation, or a combination thereof. Typical modified starches include cationic starches, hydroxyethyl starch and carboxymethylated starches. In particular embodiments, the starch is a modified starch. Exemplary modified starches include, but are not limited to, CAPSUL, CAPSUL FP, HI-CAP IMF, HI-CAP 100 and the like. In one embodiment, the aqueous starch solution optionally includes maltose, sucrose, maltodextrin, or a combination thereof. In another embodiment, the aqueous starch solution also optionally includes a cellulose ether, e.g., METHOCEL.

The oil phase includes an active material and optionally monoglycerides, lecithin, or a combination thereof. In some embodiments, an active material is also encapsulated within the microcapsule. In this respect, the microcapsule composition of this invention can include a first fragrance (encapsulated in the microcapsule) and a second fragrance (present in the oil phase that dispersed in the starch). In some embodiments, the first and second fragrances are the same. In other embodiments, the first and second fragrances are different.

In still further embodiments, the polyurea/polyurethane microcapsule suspension includes one or more additional microcapsules such as a sol-gel capsule, a hydrogel capsule, a polyurea capsule, an aminoplast capsule, a gelatin capsule, a urea-formaldehyde capsule, or a melamine-formaldehyde capsule, which encapsulates an active material, e.g., a second fragrance oil. In some embodiments, the microcapsule suspension includes a nonionic polymer (e.g., polyvinylpyrrolidone, polyvinyl alcohol, polyethylene glycol, polyethylene oxide, polyethylene oxide-polypropylene oxide, polyethylene oxide-polypropylene oxide-polyethylene oxide, or a combination thereof), cationic polymer (e.g., Polyquaternium-6, Polyquaternium-11, Polyquaternium-47, or a combination thereof), anionic polymer (e.g., a polystyrene sulfonic acid, polyacrylic acid, hyaluronic acid, sodium alginate, sodium carboxymethylcellulose, or a combination thereof), anionic surfactant (e.g., sodium laureth sulfate, complex ester of phosphoric acid and ethoxylated cosmetic grade oleyl alcohol, or a combination thereof), or a combination thereof. In other embodiments the starch/microcapsule are at a ratio in the range of 10/90 to 90/10 on a dry weight basis (e.g., 20/80 to 80/20, 30/70 to 70/30, and 40/60 to 60/40).

The spray-dried microcapsule composition thus prepared is a hybrid encapsulate formulation containing a microcapsule coated with starch or dispersed in a starch matrix. The starch coated microcapsule can have a size of 5 to 1000 µm (e.g., 10 to 300 µm). In some embodiments, the spray-dried microcapsule composition further contained an unencapsulated active material (e.g., a free fragrance) that is coated by the starch or dispersed in the starch matrix. In other embodiments, the spray-dried microcapsule composition further contains one or more additional (e.g., a second, third, fourth, fifth, or sixth) microcapsules.

These hybrid microcapsule compositions can provide variable and multistage release of active materials. The release of encapsulated active materials, such as fragrances, can be triggered either by moisture or shear to provide multi-stage release profiles. In this connection, this invention also provides a method for releasing fragrance by moisture, shear, or a combination thereof by encapsulating a first fragrance in a polyurea or polyurethane microcapsule, mixing the microcapsule with a fragrance emulsion containing a second fragrance and starch to obtain a hybrid fragrance encapsulate formulation, spray drying the hybrid fragrance encapsulate formulation to obtain a microcapsule composition, incorporating the microcapsule composition into a consumer product base to obtain a consumer product, and applying the consumer product containing the microcapsule composition to a surface, thereby releasing the first and second fragrances upon exposing the surface to moisture, shear, or a combination thereof. In some embodiments, the active materials are released in two stages. In one embodiment, the active material is first released by moisture and then by shear. In a second embodiment, the active material is first released by shear and then by moisture. The microcapsule composition can provide instant release of active materials (e.g., fragrance) by either moisture activation or shear force depending on the environments and application needs. It will also enable the release of active materials at different time points by shear. Therefore, the invention provide a system that can provide perfumery benefits at different consumer needed "magic moments" by varying release mechanism and release at different application points under a range of application environments.

As described herein, the spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g. shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

As another way to incorporate the microcapsule composition into a consumer product, the microcapsule composition in a slurry is sprayed onto a consumer product, e.g., a fabric care product. By way of illustration, a liquid delivery system containing capsules is sprayed onto a detergent powder during blending to make granules. See US 2011/0190191. In order to increase fragrance load, water-absorbing material, such as zeolite, can be added to the delivery system.

Alternatively, granulates in a consumer product are prepared in a mechanical granulator in the presence of a granulation auxiliary such as non-acid water-soluble organic crystalline solids. See WO 2005/097962.

Stabilizing Agents.

The microcapsule compositions of this invention each can contain one or more stabilizing agents to improve the stability for an extended period of storage. When one of these capsule compositions is added to a consumer product such as a liquid fabric softener/freshener and liquid detergent, this composition will also improve the viscosity stability of the consumer product, thus extend the shelf life of the product.

The stabilizing agent in the capsule composition can be present in an amount effective to stabilize the composition and/or the final consumer product containing the composition. This amount can be 1 ppm or greater (e.g., 20 ppm or greater, 20 ppm to 20%, 50 ppm to 10%, 50 ppm to 2%, 50 ppm to 1%, 50 to 2000 ppm, and 50 to 1000 ppm). Its concentration in a consumer product can be 20 ppm to 2% (e.g., 50 ppm to 2%, 50 ppm to 1%, 50 to 2000 ppm, and 50 to 1000 ppm).

Useful stabilizing agents include multi-functional amines, amino acids/peptides, mono-functional amines, polymers, and a polymeric mixture. These stabilizing agents are in presence in the compositions as free compounds, which are not covalently attached to the capsule walls, being part of the capsule walls, or encapsulated in capsules.

Multi-functional amines are those having at least an amine group (primary, secondary, or tertiary) and one or more other functional groups such as an amine and hydroxyl group. Exemplary multi-functional amines include hexamethylenediamine, hexaethylenediamine, ethylenediamine, 1,3-diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, amino-2-methyl-1-propanol branched polyethylenimine, chitosan, 1,3-diamino-guanidine, 1,1-dimethylbiguanide, and guanidine. Suitable amino acids/peptides include arginine, lysine, histidine, ornithine, nisin, and gelatin. Suitable stabilizing polymers include polyvinylpyrrolidone, polyvinylpyridine-N-oxide, and polyvinyl imidazolinium. These polymers sometimes are used in combination with a second polymer (e.g., a block copolymer) such that the second polymer.

Monofunctional amines have a single amine group. Examples include $C_1$-$C_{20}$ primary, secondary, or tertiary amines, each of which typically has a molecular weight of 30 to 800 Daltons (e.g., 31 to 500 Daltons and 31 to 300 Daltons). They can be linear, branched, cyclic, acyclic, saturated, unsaturated, aliphatic, and/or aromatic. Nonlimiting examples are methylamine, dimethylamine, trimethylamine, ethylamine, diethylamine, triethylamine, propylamine, isopropylamine, butylamine, dodecylamine, tetradecylamine, aniline, 4-methylaniline, 2-nitroaniline, diphenyl amine, pyrrolidone, piperidine, and morpholine.

Fabric Conditioning Agents.

The capsule compositions of this invention are suitable for use in personal care products, fabric care products, and home care products.

More specifically, the capsule compositions are suitable for preparing perfumed liquid fabric softeners/fresheners. It is discovered that these capsule compositions unexpectedly improve the viscosity stability of liquid fabric softeners.

At least one fabric softening agent is present in each liquid fabric softener, preferably at a concentration of 1 to 30% (e.g., 4 to 20%, 4 to 10%, and 8 to 15%). It would be obvious to a skilled person in the art to determine the concentration of a fabric softening agent while keeping its conditioning benefits and also maintaining a reasonable stability and shelf life. In addition, the ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.

Applications.

The capsule compositions of the present invention are well-suited for use, without limitation, in the following products:

a) Household products
  i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818
  ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
  iii. Scent Boosters such as those described in US 2007/0269651 A1 and US2014/0107010 A1,
  iv. Fabric Care Products such as Rinse Conditioners, Fabric Liquid Conditioners, Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134
  v. Liquid dish detergents such as those described in U.S. Pat. Nos. 6,069,122 and 5,990,065
  vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562
  vii. All-purpose Cleaners
  viii. Bathroom Cleaners
  ix. Bath Tissue
  x. Rug Deodorizers
  xi. Candles
  xii. Room Deodorizers
  xiii. Floor Cleaners
  xiv. Disinfectants
  xv. Window Cleaners
b) Household Devices
  i. Paper towels
  ii. Disposable Wipes c) Baby Care Products
   i. Diaper Rash Cream/Balm
   ii. Baby Powder
d) Baby Care Devices
   i. Diapers
   ii. Bibs
   iii. Wipes
e) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.
   i. Tooth Paste. An exemplary formulation as follows:
      1. calcium phosphate 40-55%
      2. carboxymethyl cellulose 0.8-1.2%
      3. sodium lauryl sulfate 1.5-2.5%
      4. glycerol 20-30%
      5. saccharin 0.1-0.3%
      6. flavor oil 1.0-2.5%
      7. water q.s. to 100%
         A typical procedure for preparing the formulation includes the steps of (i) mixing by a blender according to the foregoing formulation to provide a toothpaste, and (ii) adding a composition of this invention and blending the resultant mixture till homogeneous.
   ii. Tooth Powder
   iii. Oral Rinse
   iv. Tooth Whiteners
   v. Denture Adhesive
f) Hand Sanitizer
g) Antiinflammatory balms, ointment or spray
h) Health Care Devices
   i. Dental Floss
   ii. Toothbrushes
i) Feminine Hygiene Products such as Tampons, Feminine Napkins and Wipes, and Pantiliners
j) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
   i. Personal Cleansers (Bar Soap, Body Wash, Shower Gel)
   ii. Sunscreen (Spray or lotion)
   iii. Deodorants and Antiperspirants including aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant and spray deodorant.
   iv. Wax-based Deodorant. An exemplary formulation as follows:
      1. Paraffin Wax 10-20%
      2. Hydrocarbon Wax 5-10%
      3. White Petrolatum 210-15%
      4. Acetylated Lanolin Alcohol 2-4%
      5. Diisopropyl Adipate 4-8%
      6. Mineral Oil 40-60%
      7. Preservative (as needed)
         The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
   v. Glycol/Soap Type Deodorant. An exemplary formulation as follows:
      1. Propylene Glycol 60-70%
      2. Sodium Stearate 5-10%
      3. Distilled Water 20-30%
      4. 2,4,4-Trichloro-2'-Hydroxy Diphenyl Ether, manufactured by the Ciba-Geigy Chemical Company and a Trademark of the Ciba-Geigy Chemical Company) 0.01-0.5%
         The ingredients are combined and heated to 75° C. with stirring until the sodium stearate has dissolved. The resulting mixture is cooled to 40° C. followed by addition of a composition of this invention.
   vi. Lotion including Body Lotion, Facial Lotion, and Hand Lotion
   vii. Body Powder
   viii. Hand Sanitizers
   ix. Toiletries
   x. Body Spray
   xi. Shave Cream
   xii. Bath Soak
   xiii. Exfoliating Scrub
k) Personal Care Devices
   i. Facial Tissues
   ii. Cleansing wipes
l) Hair Care Products
   i. Shampoo (liquid and dry powder)
   ii. Hair Conditioner (Rinse out and leave-in)
   iii. Hair Rinses
   iv. Hair Refreshers
   v. Hair styling products, Hair Fixative and styling aids
   vi. Hair combing creams
   vii. Hair Bleaches, Dyes and Colorants m) Beauty Care
  i. Fine Fragrance—Alcoholic. Compositions and methods for incorporating fragrance capsules into alcoholic fine fragrances are described in U.S. Pat. No. 4,428,869. Alcoholic fine fragrances may contain the following:
    1. Ethanol (1-99%)
    2. Water (0-99%)
    3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.-1-%)
    4. Optionally an emulsifier or an emollient may be included including but not limited to those listed above
  ii. Solid Perfume
  iii. Liquid Foundation
  iv. Powder Foundation
  v. Eye Shadow
  vi. Lipstick/lip balm
n) Confectioneries, preferably selected from the group consisting of chocolate, chocolate bar products, other products in bar form, fruit gums, hard and soft caramels and chewing gum
  i. Gum
    1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or U.S. Pat. No. 6,986,709.) 20-25%
    2. Powdered sugar 45-50%
    3. glucose 15-17%
    4. starch syrup 10-13%
    5. plasticizer 0.1%
    6. flavor 0.8-1.2%
      The components described above were kneaded by a kneader according to the foregoing formulation to provide a chewing gum. Encapsulated Flavor or sensate is then added and blended till homogeneous.
  ii. Breath Fresheners
  iii. Orally Dissolvable Strips
  iv. Chewable Candy
  v. Hard Candy
o) Baked products, preferably selected from the group consisting of bread, dry biscuits, cakes and other cookies;
p) snack foods, preferably selected from the group consisting of baked or fried potato chips or potato dough products, bread dough products and corn or peanut-based extrudates;
  i. Potato, tortilla, vegetable or multigrain chips
  ii. Popcorn
  iii. Pretzels
  iv. Extruded stacks
q) Cereal Products preferably selected from the group consisting of breakfast cereals, muesli bars and precooked finished rice products
r) Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
  i. Ready to drink liquid drinks
  ii. Liquid Drink Concentrates
  iii. Powder Drinks
  iv. Coffee: Instant Cappucino
    1. Sugar 30-40%
    2. Milk Powder 24-35%
    3. Soluble Coffee 20-25%
    4. Lactose 1-15%
    5. Food Grade Emulsifier 1-3%
    6. Encapsulated Volatile Flavor 0.01-0.5%
  v. Tea
  vi. Alcoholic
s) Spice blends and consumer prepared foods
  i. Powder gravy, sauce mixes
  ii. Condiments
  iii. Fermented Products
t) Ready to heat foods: ready meals and soups, preferably selected from the group consisting of powdered soups, instant soups, precooked soups
  i. Soups
  ii. Sauces
  iii. Stews
  iv. Frozen entrees
u) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages
  i. Yoghurt
  ii. Ice cream
  iii. Bean Curd
  iv. Cheese
v) Soya protein or other soybean fractions, preferably selected from the group consisting of soya milk and products produced therefrom, soya lecithin-containing preparations, fermented products such as tofu or tempeh or products produced therefrom and soy sauces;
w) meat products, preferably selected from the group consisting of ham, fresh or raw sausage preparations, and seasoned or marinated fresh or salt meat products
x) Eggs or egg products, preferably selected from the group consisting of dried egg, egg white and egg yolk
y) and oil-based products or emulsions thereof, preferably selected from the group consisting of mayonnaise, remoulade, dressings and seasoning preparations
z) fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S.

Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "capsule" and "microcapsule" herein are used interchangeably.

The terms "polyfunctional isocyanate," "multifunctional isocyanate," and "polyisocyanate" all refer to a compound having two or more isocyanate (—NCO) groups.

The terms "polyfunctional amine," "multifunctional amine," and "polyamine" refers to a compound containing two or more primary or secondary amine groups. These terms also refers to a compound containing one or more primary/secondary amine groups and one or more hydroxyl groups (—OH).

The terms "polyfunctional alcohol," "multifunctional alcohol," "poly alcohol," and "polyol" refer to a compound having two or more hydroxyl groups.

All publications cited herein are incorporated by reference in their entirety.

The invention is described in greater detail by the following non-limiting examples.

Example 1

A microcapsule of this invention, i.e., Microcapsule Composition 1, was prepared following the procedure described below. This microcapsule composition contains a polyurea microcapsule wall, a microcapsule core containing a fragrance, and a mixture of Morwet D-425 and polyvinylpyrrolidone ("PVP") as the dispersant.

Step 1. An oil phase was prepared by mixing 96 grams of a model fragrance, i.e., Fragrance A, 24 g of Neobee oil (commercially available from Stepan, Chicago, Ill., USA), and 9.6 g of isocyanate monomer, Lupranate® M20 (commercially available from BASF corporation, Wyandotte, Mich., USA). In a separate beaker was prepared an aqueous solution (160 g) containing 1% Morwet D-425 (commercially available from Akzo Nobel, Fort Worth, Tex., USA; an alkylnaphthalenesulfonate formaldehyde condensate) and 1% PVP (Luviskol® K90, commercially available from BASF, Ludwigshafen, Germany). Luviskol K90 has an K value of 88-96 and an average molecular weight of 1,200,000. Subsequently, the oil phase was emulsified into the aqueous phase to form the fragrance emulsion under high shearing (Ultra Turrax®, T25 Basic, IKA® WERKE) at 9500 rpm for two minutes.

Step 2. Formation of fragrance microcapsules. The fragrance emulsion prepared in Step 1 was placed in a round bottom vessel and to which 10.8 g of 40% hexamethylene diamine ("HMDA") (commercially available from INVISTA, Wichita, Kans., USA) was added under constant mixing with an overhead mixer. Formation of microcapsules was immediately visible by using optical microscopy. The mixer speed was reduced after the addition of HMDA was complete. The microcapsule slurry was cured at 55° C. for two hours.

The microcapsule composition thus prepared contained 0.5% Morwet D-425 and 0.5% PVP by weight.

The size of the microcapsules thus prepared fell in the range of submicron (e.g., 0.1 µm) to hundreds of microns (e.g., 500 µm). The microcapsule size varies depending on the concentrations and ratios of Morwet D-425/PVP and shear rates used.

Suitable concentrations of Morwet D-425 are from 0.5 to 4%. Suitable concentration of PVP varies from 0.5% to 4%.

More microcapsule compositions of this invention can also be prepared following a procedure similar to that described above using other PVP, e.g., Luviskol® K17 (commercially available from BASF; having a K value of 17 and an average molecular weight of 9,000), Luviskol® K30 (commercially available from BASF; having a K value of 30 and an average molecular weight of 45,000), and Luviskol® K60 (commercially available from BASF; having a K value of 60 and an average molecular weight of 350,000), and Luviskol® K80 (commercially available from BASF; having a K value of 80 and an average molecular weight of 900,000). Additional suitable dispersants include polyvinyl alcohol ("PVA"), carboxymethyl cellulose ("CMC"), and polystyrene sulfonic acid ("PSS").

Example 2

A second microcapsule composition of this invention, i.e., Microcapsule Composition 2, was prepared following the same procedure described in Example 1 except that a second model fragrance, i.e., Fragrance B, was used instead of Fragrance A.

Example 3

A third microcapsule composition, i.e., Microcapsule Composition 3, was prepared following the same procedure described in Example 2, except that different amounts of Morwet D-425 and PVP were used. Microcapsule Composition 3 contained 0.25% Morwet D-425 and 0.5% PVP by weight of the composition.

Example 4

A fourth microcapsule composition, i.e., Microcapsule Composition 4, was prepared following the same procedure described in Example 2, except that different amounts of Morwet D-425 and PVP were used. Microcapsule Composition 3 contained 0.5% Morwet D-425 and 1% PVP by weight of the composition.

Example 5

A fifth microcapsule composition of this invention, i.e., Microcapsule Composition 5, was prepared following the same procedure described in Example 1 except that a third model fragrance, i.e., Fragrance C, was used instead of Fragrance A.

Example 6

A sixth microcapsule composition of this invention, i.e., Microcapsule Composition 6, was prepared following the procedure below.

Microcapsule Composition 5 described above was mixed with 35.5 grams 2% Lupamin 9095 (polyvinylamine having a molecular weight of 340,000 Da, commercially available from BASF) under constant mixing with an overhead mixer. Consequently, 37.2 grams of an alginate solution was added and homogenized under mixing at 3500 RPM for 1 minute. The resultant slurry was further aged at room temperature for 4 hours. Under mixing at 300 RPM, 18.6 grams of 0.1% $Na_2SO_4$ aqueous solution was added. The pH of the slurry was adjusted to pH 7.5 using lactic acid to obtain Microcapsule Composition 6.

Example 7

Another microcapsule composition of this invention, i.e., Microcapsule Composition 7, was prepared by mixing Microcapsule Composition 5 with 12.8 grams of 2% Lupamin 9095 and 9 grams of 5% Merquat 100 (PQ-6).

Example 8

An eighth microcapsule composition of this invention, i.e., Microcapsule Composition 8, was prepared by mixing Microcapsule Composition 5 with 34 grams of 2% Carbopol ETD 2050 (crosslinked polyacrylic acid polymer; commercially available from Lubrizol, Wickliffe, Ohio). The pH of the slurry was adjusted to 8 by citric acid.

Examples 9-14

Six more microcapsule compositions of this invention, i.e., Microcapsule Compositions 9-14, were prepared following the procedure below.

These microcapsule compositions were spray dried hybrid fragrance encapsulation formulations.

Preparation of Part A. Part A was prepared by weighing out the desired amount of water and CAPSUL Starch (National Starch, Bridgewater, N.J.) into a suitable container. The mixture was then heated to 50-55° C. and Maltose (Mitsubishi, Japan) and METHOCEL cellulose ethers (Dow Chemical, Middle Land, Mich.) were added. The mixture was kept at 55° C. and stirred with an overhead mixer until a homogeneous solution was obtained. Part A was cooled to 19° C. by submersion it in an ice bath to prevent pre-mature volatilization of fragrance ingredients.

Preparation of Part B. Part B was prepared by weighing out the desired amount of DIMODAN PH320 (distilled monoglyceride; Dow Chemical, Middle Land, Mich.) and heating until the material was liquefied. The desired amount of a model fragrance, i.e., Fragrance D, was then added with constant mixing until a homogenous phase was obtained.

Preparation of Part C. Part C was prepared by dissolving solid LUVISKOL K30 into water to obtain a 30% LUVISKOL K-30 (Polyvinylpyrrolidone; BASF) aqueous solution, which was then added to a Microcapsule Composition 5 slurry under constant stirring. The mixing continued for 30 minutes to ensure a homogenous mixture was obtained.

Preparation of Fragrance Emulsion. A fragrance emulsion was prepared by adding Part B or fragrance oil into Part A followed by emulsifying with a high shear homogenizer (Greerco, Model 11, 2001 with Baldor Industrial Motor) in an ice-bath. The prepared emulsion had a particle size of 3 microns or less.

Preparation of Solution for Spray Drying. The mixture of Part C was combined with the fragrance emulsion under consistent stirring with an overhead mixer. This mixture was then fed into a Niro Spray Drier. The inlet temperature was maintained at 190° C. and the emulsion was fed at a rate sufficient to maintain an exit air temperature at 90° C.

Formulations containing different ratios of fragrance emulsion to microcapsule slurry were prepared, each containing a 45.1% fragrance load. Microcapsule Composition 9 (Table 3; 90/10 ratio) and Microcapsule Composition 10 (Table 4; 70/30 ratio) were obtained using the materials shown in the tables. Microcapsule Composition 11 (Table 5; 90/10 ratio) and Microcapsule Composition 12 (Table 6; 70/30 ratio) were prepared following the procedure described above except that the fragrance was added directly to the starch solution. Microcapsule Composition 13 (Table 7; 90/10 ratio) and Microcapsule Composition 14 (Table 8; 70/30 ratio) were prepared following the same procedure except that the fragrance was added directly to the starch solution containing HI-CAP 100 (modified food starch derived from waxy maize).

In the context of this invention, the ratio of starch/microcapsule is defined as the dry weight of starch to that of the microcapsule suspension minus the amount of water in the suspension. Thus, the dry weight of the microcapsule is the cumulative weight of the capsule wall polymer, the oil/fragrance core, and the capsule formation aid used in preparing the microcapsule.

TABLE 3

| Part | Ingredient | Parts* | Dry Weight (%) |
|---|---|---|---|
| A | Water | 880 | |
| | CAPSUL Starch | 416 | 41.6 |
| | Maltose | 41.2 | 4.12 |
| | METHOCEL A4M | 23 | 2.3 |
| B | DIMODAN PH 320 | 17 | 1.7 |
| | Fragrance | 382.8 | 38.28 |
| C | LUVISKOL K-30 30% soln | 20 | 2 |
| | Polyurea capsule slurry | 100 | 10 |
| | Total Solid Input: | 1000 | 100 |

*Unit: grams

TABLE 4

| Part | Ingredient | Parts* | Dry Weight (%) |
|---|---|---|---|
| A | Water | 665 | |
| | CAPSUL Starch | 383.5 | 38.35 |
| | Maltose | 46 | 4.6 |
| | METHOCEL A4M | 23 | 2.3 |
| B | DIMODAN PH 320 | 13 | 1.3 |
| | Fragrance | 199.5 | 19.95 |
| C | LUVISKOL K-30 30% soln | 35 | 3.5 |
| | Polyurea capsule slurry | 300 | 30 |
| | Total Solid Inputs: | 1000 | 100 |

*Unit: grams

TABLE 5

| Part | Ingredient | Parts* | Dry Weight (%) |
|---|---|---|---|
| A | Water | 834 | |
|   | Capsule Starch | 452 | 45.2 |
|   | Maltose | 46 | 4.6 |
|   | Fragrance | 382 | 38.2 |
| B | LUVISKOL K-3G 30% soln | 20 | 2 |
|   | Polyurea capsule slurry | 100 | 10 |
|   | Total Solid Inputs: | 1000 | 100 |

*Unit: grams

TABLE 6

| Part | Ingredient | Parts* | Dry Weight (%) |
|---|---|---|---|
| A | Water | 665 | |
|   | Capsule Starch | 411.5 | 41.15 |
|   | Maltose | 54 | 5.4 |
|   | Fragrance | 199.5 | 19.95 |
| B | LUVISKOL K-30 30% soln | 35 | 3.5 |
|   | Polyurea capsule slurry | 300 | 30 |
|   | Total Solid Inputs: | 1000 | 100 |

*Unit: grams

TABLE 7

| Part | Ingredient | Parts* | Dry Weight (%) |
|---|---|---|---|
| A | Water | 880 | |
|   | HI-CAP 100 | 498 | 49.8 |
|   | Fragrance | 382 | 38.2 |
| B | LUVISKOL K-30 30% soln | 20 | 2 |
|   | Polyurea capsule slurry | 100 | 10 |
|   | Total Solid Inputs: | 1000 | 100 |

*Unit: grams

TABLE 8

| Part | Ingredient | Parts* | Dry Weight (%) |
|---|---|---|---|
| A | Water | 665 | |
|   | HI-CAP 100 | 415 | 41.5 |
|   | Fragrance | 250 | 25 |
| B | LUVISKOL K-30 30% soln | 35 | 3.5 |
|   | Polyurea capsule slurry | 300 | 30 |
|   | Total Solid Inputs: | 1000 | 100 |

*Unit: grams

Comparative Study

No microcapsule could be prepared using PVP alone as the dispersant.

The same procedure described in Example 2 was followed except that PVP (1% in the aqueous solution) was used instead of a mixture of Morwet D-425 and PVP.

After the curing step, a fragrance oil was observed on the top of the reaction mixture, indicating that microcapsules were not formed.

Comparative Compositions

Two comparative compositions, i.e., Comparatives 1 and 2, were prepared, as described separately below.

Comparative 1 was prepared following the same procedure described above except that no PVP was used. The comparative microcapsule composition contains a polyurea microcapsule wall, a microcapsule core containing the fragrance as Microcapsule Composition 1, and Morwet D-425 as the dispersant.

Comparative 2 was prepared following the same procedure described in Example 2 except that the dispersant is Morwet D-425, instead of the mixture of Morwet D-425 and PVP.

Example 15

Each of microcapsule Compositions 1-4 and Comparative 1-2 was evaluated for fragrance delivery performance in an EU fabric conditioner base.

More specifically, one of the compositions was bended with an EU model fabric conditioner at a fragrance load of 0.5% neat oil equivalent to obtain a fragranced conditioner. Laundry experiments were conducted following a standard experimental protocol with an European wash machine. Terry towels were washed with the fragranced conditioner. Damp towels were then removed from the machine and evaluated by a panel of 12 judges. The fragrance intensity is rated at a scale ranging from 0 to 35. A numerical value of 4 would suggest that the towel being evaluated produces a weak intensity while a value of 30 would indicate that the towel generates a very strong smell. The results are shown in Tables 9 and 10 below.

As seen in Table 9, Microcapsule Composition 1 had a fragrance intensity of 10.9 at the damp stage, which is unexpectedly more than 1.8 folds that of its corresponding comparative composition, i.e., Comparative 1. Note that Comparative 1 was prepared following the same procedure as Microcapsule Composition 1 except that an alkylnaphthalenesulfonate formaldehyde condensate was used instead of a mixture of PVP and the alkylnaphthalenesulfonate formaldehyde condensate.

Table 10 shows that Microcapsule Compositions 2-4 each had a fragrance intensity (at the damp stage) of 11.4, 11.3, and 11.7, respectively. On the other hand, the corresponding comparative composition, i.e., Comparative 2, had a fragrance intensity (also at the damp stage) of 8. Unexpectedly, Microcapsule Compositions 2-4 of this invention had a fragrance intensity at least 1.4 folds that of Comparative 2.

TABLE 9

| Sample | Damp intensity |
|---|---|
| Microcapsule Composition 1 | 10.9 |
| Comparative 1 | 5.9 |

TABLE 10

| Sample | Damp intensity |
|---|---|
| Microcapsule Composition 2 | 11.4 |
| Microcapsule Composition 3 | 11.3 |
| Microcapsule Composition 4 | 11.7 |
| Comparative 2 | 8 |

Other than the fabric conditioner formulation, microcapsule compositions of this invention can also be used in many personal or house care products. Exemplary products are illustrated in the examples below.

Example 16. Clear Deodorant Stick Formulation

An exemplary clear deodorant stick formulation is provided in Table 11

TABLE 11

| Ingredient | Percentage |
| --- | --- |
| Water | q.s. 100* |
| Phosphatidylglycerol/Diphosphatidylglycerol | 55 |
| Sodium Stearate | 6 |
| PEG-4 | 15 |
| Antibacterial Agent | 0.1 |
| Microcapsule Composition | 1-10 |

*The amount needed to bring the total percentage to 100.

Example 17. Antiperspirant Emulsion Spray Formulation

Provided in Table 12 below is an exemplary antiperspirant emulsion spray formulation.

TABLE 12

| Ingredient | Percentage |
| --- | --- |
| Water | q.s. 100 |
| Dimethicone | 6 |
| Aluminum Chlorohydrate | 5-6 |
| EDTA | 0.15 |
| Lauryl PEG-9 Polydimethylsiloxyethyl Dimethicone | 0.3 |
| Phenoxyethanol | 0.3 |
| Isobutane | 70 |
| Microcapsule Composition | 1-10 |

Example 18. Antiperspirant Emulsion Roll-On Formulation

Provided in Table 13 below is an exemplary antiperspirant emulsion roll-on formulation.

TABLE 13

| Ingredient | Percentage |
| --- | --- |
| Water | q.s. 100 |
| Aluminum Chlorohydrate or Aluminum Zirconium Tetrachlorohydrex Gly | 32-36 |
| Steareth-2, Steareth-20 | 0.5-4 |
| Silica | 1-5 |
| Glycerin | 3-5 |
| Dimethicone | 0.5 |
| Microcapsule Composition | 1-10 |

Example 19. Antiperspirant Clear Emulsion Stick Formulation

Provided in Table 14 below is an exemplary antiperspirant clear emulsion stick formulation.

TABLE 14

| Ingredient | Percentage |
| --- | --- |
| Water | q.s. 100 |
| Aluminum Zirconium Tetrachlorohydrex Gly | 20 |
| Stearyl Alcohol | 30 |
| C12-C15 Alkyl Benzoate | 25 |
| Glycine | 7 |
| Dimethicone | 0.07 |
| Microcapsule Composition | 1-15 |

Example 20. Antiperspirant Opaque Emulsion Stick Formulation

Provided in Table 15 below is an exemplary antiperspirant opaque emulsion stick formulation.

TABLE 15

| Ingredient | Percentage |
| --- | --- |
| Water | q.s. 100 |
| Aluminum Chlorohydrate | 40 |
| Isopropyl Palmitate | 9 |
| Dimethicone | 5.8 |
| Synthetic Wax | 9 |
| Beheneth-10 | 2 |
| Polyglyceryl-3 Diisosterate | 0.3 |
| Acrylates Copolymer | 0.3 |
| PEG/PPG-18/18 Dimethicone | 2 |
| Phenoxyethanol | 0.5 |
| Pentylene Glycol | 0.5 |
| Cetyl PEG/PPG-10/1 Dimethicone | 2 |
| Microcapsule Composition | 1-10 |

Example 21. Deodorant Spray Formulation

Provided in Table 16 below is an exemplary deodorant spray formulation.

TABLE 16

| Ingredient | Percentage |
| --- | --- |
| Denatured Alcohol | q.s. 100 |
| Polyaminopropyl biguanide stearate | 0.2-0.5 |
| Butane, Isobutane, Propane, 152A | 55 |
| Microcapsule Composition | 1-10 |

Example 22. Antiperspirant Clear Gel Formulation

Provided in Table 17 below is an exemplary antiperspirant clear gel formulation.

TABLE 17

| Ingredient | Percentage |
| --- | --- |
| Water | q.s. 100 |
| Aluminum Zirconium Tetrachlorohydrex Gly | 25 |
| Silicone | 40 |
| Phosphatidylglycerol | 10 |
| Emulsifier | 10 |
| Microcapsule Composition | 1-10 |

Example 23. Deodorants and Antiperspirants

Described below is preparation of an exemplary wax-based deodorant by mixing paraffin wax (10-20%), hydrocarbon was (5-10%), white petrolatum (10-15%), acetylated lanolin alcohol (2-4%), diisopropyl adipate (4-8%), Mineral Oil (40-60%) and preservative (as needed); heating the mixture to 75° C. until melted, and, with stirring at 75° C., adding 4 wt % of a microcapsule composition of this invention.

An exemplary glycol/soap type deodorant is prepared by combining propylene glycol (60-70%), sodium stearate (5-10%), distilled water (20-30%) and 2,4,4-trichloro-2'-hydroxy diphenyl ether (0.01-0.5%); and heating the mixture, with stirring, to 75° C. until the sodium stearate has dissolved. The resulting mixture is cooled to 40° C. and a microcapsule composition is added to the formulation.

An exemplary antiperspirant deodorant (soft solid) is prepared by combining cyclopentasiloxane (60%), dimethicone (10%), zirconium aluminum trichlorohydrex glycine (25%), a microcapsule composition (2.5%) and fumed silica (2.5%).

Example 24. Body Wash

An exemplary body wash is composed of PLANTAPON 611 L (SLES, Cap Betaine, Lauryl Glycoside; 22%), ammonium lauryl sulfate (2.5%), LAMESOFT OP65 (Coco Glucoside, Glyceryl Oleate; 3%), polyquaternium 10-10 (0.5%), acrylates copolymer (0.5%), neat fragrance (0.3%), a microcapsule composition of this invention (1%), DMDM hydantoin (0.3%), glycerin (3%) and water (q.s. 100%).

Example 25. Hair Products

An exemplary 2-in-1 hair shampoo is composed of sodium laureth sulfate (10%), cocamidopropyl betaine (7%), glyceryl stearate (2%), cetearyl alcohol (3%), panthenol (0.2%), acrylates copolymer (1.2%), dimethicone (1.5%), polyquaternium 10 (0.2%), a microcapsule composition of this invention (1%), preservative (as needed), water (q.s. 100%), and NaOH to pH 6.0.

An exemplary hair gel is compose of PVP (3%), acrylates/C10-30 alkyl methacrylate copolymer (3%), denatured alcohol (10%), a microcapsule composition of this invention (1%), Microcare PHG (0.5%), and water (q.s. 100%).

Example 26. Lotion

An exemplary lotion is composed of glyceryl stearate-SE (7%), sweet almond oil (4%), sunflower oil (4%), avocado oil (2%), acrylates copolymer (0.3%), a microcapsule composition of this invention (1%), preservative (1%), glycerin (4%), and water (q.s. 100%).

Example 27. Talc-Free Dusting Powder

An exemplary dusting powder is composed of mica (50%), corn starch (45%), potassium sorbate (0.25%), sodium benzoate (0.25%) and a microcapsule composition of this invention (2.5%).

Example 28. Lip Balm

An exemplary lip balm is composed of the following: sunflower oil (50%), sweet almond oil (20%), avocado oil (10%), a microcapsule composition of this invention (2%), beeswax (7%), candilla wax (4%), carnuba wax (4%), caprylyl glycol (1%), and peppermint oil (2%).

Example 29. Hand Sanitizer

An exemplary hand sanitizer is composed of acrylates C10-30 alkyl acrylate copolymer (0.2-0.5%), ethanol (60%), isopropanol (10%), glycerin (4%), a microcapsule composition of this invention (1-5%), and water (q.s. 100%).

Example 30. Fine Fragrance

An exemplary fine fragrance (alcoholic) can include ethanol (1-99%); water (0-99%); a suspending aide including, but not limited to, hydroxypropyl cellulose, ethyl cellulose, silica, microcrystalline cellulose, carrageenan, propylene glycol alginate, methyl cellulose, sodium carboxymethyl cellulose or xanthan gum (0.1%); and optionally an emulsifier or an emollient. To this is added a microcapsule composition of this invention. Compositions and methods for incorporating fragrance capsules into alcoholic fine fragrances are described in U.S. Pat. No. 4,428,869.

Example 31. Performance of Microcapsule Composition in a Hair Conditioner Base

To evaluate its performance, Microcapsule Composition 6 was blended into a model hair conditioner base. The hair conditioner typically contains: EDTA, 0.1 to 0.3%; cetyl alcohol, 1 to 4%; stearyl alcohol, 1 to 4%; behentrimonium Methosulfate (and) Cetearyl Alcohol, 2-7%; silicone fluid, 1-4%; preservative, 0.1 to 1%; neutralizing acid/bade, 0.10 to 1%; and water. The fragrance load was 0.5% neat equivalent. A comparative formulation was prepared using melamine-formaldehyde (MF) capsules described in US2007/0138671 at 0.5%. The perfumery benefit of the capsules was evaluated by conducting a personal wash experiment using a standard experimental protocol. Hair swatches were washed with one of the formulations and then air-dried overnight before being evaluated by a panel of 12 judges. The fragrance intensity is rated from a scale ranging from 0 to 10. A numerical value of 2 would suggest the hair only produce weak intensity while a value of 10 indicates the subject generate a very strong smell.

Unexpectedly, polyurea formulations using the compositions prepared in Examples 6 had a much greater fragrance intensity than the MF formulation, also both in the brushed and un-brushed tests. The results are in Table 18.

TABLE 18

| Samples | Pre-brushing intensity | Post-brushing intensity |
| --- | --- | --- |
| Composition 6 | 1.93 | 4.43 |
| MF control | 0.29 | 1.71 |

Example 32. Performance of Microcapsule Composition in a Shower Gel Base

Microcapsule Composition 7 was blended into a model shower gel solution to evaluate its performance. The shower gel personal wash base typically contains: sodium laureth sulfate, 5 to 20%; cocamidopropylbetaine, 3 to 10%; glycol distearate & laureth 4 & cocamidopropylbetaine, 1 to 10%; polyquaternium-7, 0 to 3%; DMDM Hydantoin, 0 to 3%; panthenol, 1 to 10%; sodium chloride, 0.1 to 10%; tetrasodium EDTA, 0 to 2% and water. The fragrance load was 1% mat equivalent. For comparison, similar solutions were prepared using neat fragrance at 1%. The perfumery benefit of the capsules was evaluated by conducting a standard experimental protocol. The bases were washed on panelist's forearms and dried before being evaluated by panel of 12 judges. The fragrance intensity is rated from a scale ranging from 0 to 35. A numerical value of 5 would suggest the fabric only produce weak intensity while a value of 35 indicates the subject generate a very strong smell. The results are in Table 19.

TABLE 19

| Samples | Pre-rubbing intensity | Post-rubbing intensity | $I_{pre-rubbing}/I_{post-rubbing}$ |
|---|---|---|---|
| Composition 7 | 5.9 | 8.4 | 1.42 |
| Neat oil | 4.1 | 4.2 | 1.02 |

It is clear that Microcapsule Composition 7 produced greater fragrance intensity than neat oil control samples in the model personal wash base at post-rubbing stages stage.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of preparing a stable capsule composition, one skilled in the art can prepare suitable capsules using different polyisocyanates, cross-linking agents, starch, free fragrance, and/or capsule formation aids/catalysts, varying the concentrations of these wall-forming materials and/or catalysts to achieve desirable organoleptic or release profiles in a consumable product. Further, the ratios among polyisocyanates, cross-linking agents, capsule forming aids, adjuvents, core modifiers, active materials, catalysts, PVP, and the alkylnaphthalenesulfonate formaldehyde condensate can also be determined by a skilled artisan through assays known in the art to prepare capsule compositions with desirable properties. A skilled person can also choose a suitable stabilizing agent and determine its concentration in a capsule composition and final product.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A microcapsule composition comprising
    a polyurea microcapsule,
    an alkylnaphthalenesulfonate formaldehyde condensate, and
    polyvinylpyrrolidone,
wherein
    the microcapsule has a microcapsule core containing an active material and a microcapsule wall formed of a polyurea,
    the microcapsule wall encapsulates the microcapsule core,
    the polyurea is a reaction product of a polyfunctional isocyanate and a polyfunctional amine in the presence of an alkylnaphthalenesulfonate formaldehyde condensate and polyvinylpyrrolidone,
    each of the alkylnaphthalenesulfonate formaldehyde condensate and polyvinylpyrrolidone constitutes 0.1% to 5% by weight of the microcapsule composition, and
    the weight ratio between the alkylnaphthalenesulfonate formaldehyde condensate and polyvinylpyrrolidone is 10:1 to 1:10.

2. The microcapsule composition of claim 1, wherein the polyfunctional isocyanate is an aromatic polyfunctional isocyanate, aliphatic polyfunctional isocyanate, or combination thereof, the aromatic polyfunctional isocyanate containing a phenyl, tolyl, xylyl, naphthyl, or diphenyl moiety, or a combination thereof and the aliphatic polyfunctional isocyanate being a trimer of hexamethylene diisocyanate, a trimer of isophorone diisocyanate, a biuret of hexamethylene diisocyanate, or a combination thereof.

3. The microcapsule composition of claim 2, wherein the aromatic polyfunctional isocyanate is selected from the group consisting of polymeric methylene diphenyl diisocyanate, polyisocyanurates of toluene diisocyanate, trimethylol propane-adducts of toluene diisocyanate, trimethylol propane-adducts of xylylene diisocyanate, and a combination thereof and the aliphatic polyfunctional isocyanate is selected from the group consisting of dimers, biurets, symmetric trimers, asymmetric trimers of hexamethylene diisocyanate, and a combination thereof.

4. The microcapsule composition of claim 1, wherein the polyfunctional amine is hexamethylene diamine, hexaethylenediamine, ethylenediamine, 1,3-diaminopropane, 1,4-diamino-butane, diethylenetriamine, pentaethylenehexamine, 1,6-diaminohexane, hydrazine, 1,4-diaminocyclohexane and 1,3-diamino-1-methylpropane, bis(3-aminopropyl) amine, bis(hexanethylene)triamine, tris(2-aminoethyl) amine, triethylene-tetramine, N,N'-bis(3-aminopropyl)-1,3-propanediamine, tetraethylenepentamine, branched polyethylenimine, chitosan, nisin, gelatin, 1,3-diaminoguanidine, 1,1-dimethylbiguanide, guanidine, arginine, lysine, ornithine, histidine, amino-2-methyl-1-propanol, or a combination thereof.

5. The microcapsule composition of claim 1, wherein the active material is a fragrance, pro-fragrance, flavor, malodor counteractive agent, anti-inflammatory agent, anesthetic, analgesic, anti-viral agent, anti-infectious agent, anti-acne agent, skin lightening agent, insect repellant, emollient, skin moisturizing agent, vitamin or derivative thereof, nanometer to micron size inorganic solid, polymeric or elastomeric particle, or combination thereof.

6. The microcapsule composition of claim 1, wherein each of the alkylnaphthalenesulfonate formaldehyde condensate and polyvinylpyrrolidone constitutes 0.1 to 0.2% to 3% by weight of the microcapsule composition, the ratio between the alkylnaphthalene-sulfonate formaldehyde condensate and polyvinylpyrrolidone is 2:1 to 1:4, and the polyvinylpyrrolidone has a molecular weight of 1,000 to 10,000,000.

7. The microcapsule composition of claim 1, the composition further comprising a polyvinyl alcohol, polystyrene sulfonate, carboxymethyl cellulose, copolymer of vinyl pyrrolidone and quaternized dimethylaminoethyl methacrylate, or mixture thereof.

8. The microcapsule composition of claim 1, the composition further comprising a stabilizing agent selected from the group consisting of hexamethylene diamine, hexaethylenediamine, ethylenediamine, 1,3-diaminopropane, 1,4-diamino-butane, diethylenetriamine, pentaethylenehexamine, bis(3-aminopropyl)amine, bis(hexanethylene)triamine, tris (2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, and a combination thereof.

9. The microcapsule composition of claim 1, the composition further comprising a deposition aid that is an anionic, cationic, nonionic or zwitterionic polymer.

10. The microcapsule composition of claim 1, the composition further comprising one or more free fragrances or one or more additional microcapsules, the one of more additional microcapsules are different from each other.

11. The microcapsule composition of claim 1, wherein the composition is a slurry or in a dry form.

12. The microcapsule composition of claim 1, wherein the microcapsule is coated with a starch.

13. A process of preparing a microcapsule composition of claim 1, the process comprising the steps of:
preparing an oil phase having an active material and a multi-functional isocyanate;
preparing an aqueous phase having (i) an alkylnaphthalenesulfonate formaldehyde condensate and (ii) polyvinylpyrrolidone;
emulsifying the oil phase into the aqueous phase to form an active emulsion;
adding to the active emulsion a crosslinking agent that is a polyfunctional amine to form a reaction emulsion;
causing formation of polyurea or microcapsules in the reaction emulsion to obtain a microcapsule slurry; and
curing the microcapsule slurry,
thereby obtaining a microcapsule composition of claim 1, wherein each of the alkylnaphthalenesulfonate formaldehyde condensate and polyvinylpyrrolidone constitutes 0.1% to 5% by weight of the microcapsule composition, and the weight ratio between the alkylnaphthalenesulfonate formaldehyde condensate and polyvinylpyrrolidone is 10:1 to 1:10.

14. A consumer product comprising a microcapsule composition of claim 1.

15. The consumer product of claim 14, wherein the consumer product is a shampoo, a hair conditioner, a hair rinse, a hair refresher, a hair fixative or styling aid, a hair bleach, a hair dye or colorant, a soap, a body wash, a cosmetic preparation, an all-purpose cleaner, a bathroom cleaner, a floor cleaner, a window cleaner, a bath tissue, a paper towel, a disposable wipe, a diaper rash cream or balm, a baby powder, a diaper, a bib, a baby wipe, an oral care product, a tooth paste, an oral rinse, an tooth whitener, a denture adhesive, a chewing gum, a breath freshener, an orally dissolvable strips, a chewable candy, a hard candy, a hand sanitizer, an anti-inflammatory balm, an anti-inflammatory ointment, an anti-inflammatory spray, a health care device, a dental floss, a toothbrush, a tampon, a feminine napkin, a personal care product, a sunscreen lotion, a sunscreen spray, a wax-based deodorant, a glycol type deodorant, a soap type deodorant, a facial lotion, a body lotion, a hand lotion, a body powder, a shave cream, a bath soak, an exfoliating scrub, a foot cream, a facial tissue, a cleansing wipe, a fabric care product, a fabric softener, a fabric refresher, an ironing water, a liquid laundry detergent, a liquid dish detergent, an automatic dish detergent, a unit dose tablet or capsule, a scent booster, a drier sheet, a fine fragrance, a solid perfume, a powder foundation, a liquid foundation, an eye shadow, a lipstick or lip balm, an Eau De Toilette product, a deodorant, a rug deodorizer, a candle, a room deodorizer, a disinfectant, an aerosol antiperspirant, a stick antiperspirant, a roll-on antiperspirant, an emulsion spray antiperspirant, a clear emulsion stick antiperspirant, a soft solid antiperspirant, an emulsion roll-on antiperspirant, a clear emulsion stick antiperspirant, an opaque emulsion stick antiperspirant, a clear gel antiperspirant, a clear stick deodorant, a spray deodorant, a baked product, a bread, a dry biscuit, a cake, a cookie, a chip, a popcorn, a pretzel, an extruded snack, a breakfast cereal, a muesli bar, a precooked finished rice product, an alcoholic or non-alcoholic beverage, a spice blend, a soup, a sauce, a stew, a frozen entrée, a yogurt, an ice cream, a bean curd, a cheese, a soya protein product, a meat product, an egg product, a mayonnaise, a remoulade, a dressing, a seasoning preparation, a fruit preparation, or a vegetable preparation.

\* \* \* \* \*